(12) United States Patent
Moses et al.

(10) Patent No.: US 7,632,797 B2
(45) Date of Patent: Dec. 15, 2009

(54) WATER-STABILIZED ANTIMICROBIAL ORGANOSILANE PRODUCTS, COMPOSITIONS, AND METHODS FOR USING THE SAME

(75) Inventors: Timothy C. Moses, Atlanta, GA (US); Robert McMahon, Atlanta, GA (US)

(73) Assignee: Vitec Speciality Chemicals Limited, London (GB)

( * ) Notice: Subject to any disclaimer, the term of this patent is extended or adjusted under 35 U.S.C. 154(b) by 126 days.

(21) Appl. No.: 11/680,926

(22) Filed: Mar. 1, 2007

(65) Prior Publication Data
US 2007/0237901 A1    Oct. 11, 2007

Related U.S. Application Data

(60) Provisional application No. 60/778,311, filed on Mar. 2, 2006.

(51) Int. Cl.
*C11D 3/48* (2006.01)
*C11D 1/645* (2006.01)
*C11D 3/43* (2006.01)

(52) U.S. Cl. .............. 510/384; 510/199; 510/218; 510/238; 510/245; 510/247; 510/253; 510/362; 510/432; 510/466; 510/504

(58) Field of Classification Search ............ 510/199, 510/218, 238, 245, 247, 253, 362, 384, 432, 510/466, 504
See application file for complete search history.

(56) References Cited

U.S. PATENT DOCUMENTS

| | | | |
|---|---|---|---|
| 5,411,585 A * | 5/1995 | Avery et al. ............ 106/287.1 |
| 6,113,815 A | 9/2000 | Elfersy et al. |
| 6,469,120 B1 | 10/2002 | Elfersy et al. |
| 2002/0002125 A1 * | 1/2002 | Colurciello, Jr. et al. .... 510/238 |
| 2003/0073600 A1 * | 4/2003 | Avery et al. ................ 510/382 |
| 2003/0109395 A1 * | 6/2003 | Neumiller .................. 510/246 |
| 2006/0258768 A1 * | 11/2006 | Uchiyama et al. .......... 523/102 |
| 2007/0065475 A1 * | 3/2007 | Elfersy ...................... 424/405 |

FOREIGN PATENT DOCUMENTS

WO    WO 00/56580    9/2000

* cited by examiner

*Primary Examiner*—Charles I Boyer
(74) *Attorney, Agent, or Firm*—Saliwanchik, Lloyd & Saliwanchik

(57) ABSTRACT

The present invention relates to water-stable compositions and compounds formed by mixing an organosilane, optionally having a non-hydrolyzable organic group, but having one or more hydrolyzable groups, and an acidified stabilizing solution prepared from at least one acid, at least one glycol ether, and at least one cationic surfactant, preferably at least one quaternary ammonium salt (QAS), in water. The present invention also relates to methods of treating a substrate by mixing or contacting the substrate with the product, compound, or composition of this invention for a period of time sufficient for treatment of the substrate, methods of antimicrobially treating a food article, methods of antimicrobially coating a fluid container, methods of dyeing and treating a substrate, and methods of antimicrobially coating a latex medical article. The invention also pertains to a treated substrate having adhered thereto the product, compound, or composition of this invention.

19 Claims, No Drawings

WATER-STABILIZED ANTIMICROBIAL ORGANOSILANE PRODUCTS, COMPOSITIONS, AND METHODS FOR USING THE SAME

CROSS-REFERENCE TO RELATED APPLICATION

This application claims the benefit under 35 U.S.C. §119 of U.S. Provisional Patent Application Ser. No. 60/778,311, filed Mar. 2, 2006, which is incorporated herein by reference in its entirety.

FIELD OF THE INVENTION

The invention relates to antimicrobial organosilane compositions, compounds, products, and methods for their use. In particular, this invention provides water-stable antimicrobial organosilane compounds stabilized with an acidified stabilized solution prepared from at least one quaternary ammonium salt, at least one glycol ether, and water, products, and compositions for treating various substrates; articles treated with the compounds, products, and compositions; and methods of treatment using the compounds, products, and compositions.

BACKGROUND

Organosilanes of the general formula $R_n SiX_{4-n}$ where n is an integer from 0 to 3, but more generally from 0 to 2 (where when n is 3, the organosilanes may only dimerize); R is a non-hydrolyzable organic group, such as, but not limited to, alkyl, aromatic, organofunctional, or a combination thereof, and X is alkoxy, such as methoxy or ethoxy, are prone to self-condensation rendering such organosilanes unstable in water over commercially relevant periods of time. Additionally, X can be a halogen, such as Cl, Br, or I, and is similarly liberated as HCl, HBr, or HI, For such organosilanes, the X moiety reacts with various hydroxyl containing molecules in aqueous media to liberate methanol, ethanol, HCl, HBr, HI, $H_2O$, acetic acid, or an unsubstituted or substituted carboxylic acid and to form the hydroxylated, but condensation-prone compound.

For organosilanes $R_n SiX_{4-n}$, where n is an integer from 0 to 2, hydrolysis of the first two X groups with water produces a species bearing —$Si(OH)_2$— units that can self-condense through the hydroxyl moieties to linear and/or cyclic oligomers possessing the partial structure HO—Si—(O—Si)$_{mm}$—O—Si—O—Si—O—Si—OH, where mm is an integer such that an oligomer is formed. For those cases, $RSiX_3$, hydrolysis of the third X group generates a silanetriol ($RSi(OH)_3$), which produces insoluble organosilicon polymers through linear and/or cyclic self-condensation of the Si(OH) units. This water induced self-condensation generally precludes storage of most organosilanes $R_n SiX_{4-n}$, where n ranges from 0 to 2, inclusive, in water. Except for some organosilanes that are stable in very dilute solutions at specific pH ranges, the use of water solutions of most organosilanes require the use of freshly prepared solutions.

One commercially relevant example of an organosilane suffering from such undesirable self-condensation is the antimicrobial Dow Corning 5700 (Dow Corning Corporation, Midland, Mich.). The literature describes the active ingredient of Dow Corning 5700 as 3-(trimethoxysilyl)propyl-dimethyloctadecyl ammonium chloride. However, in aqueous media, it is believed that the correct active ingredient is more likely 3-(trihydroxysilyl)propyl-dimethyloctadecyl ammonium chloride. Nonetheless, Dow Corning 5700 is a water activated antimicrobial integrated system that is capable of binding to a wide variety of natural and synthetic substrates, including fibers and fabrics, to produce a durable surface or fabric coating. 3-(Trimethoxysilyl)propyl-dimethyloctadecyl ammonium chloride is prepared by quaternization of dimethyloctadecylamine with 3-chloropropyl trimethoxysilane.

The $C_{18}$ hydrocarbon chain quaternary ammonium portion of the molecule possesses long-acting antimicrobial properties and provides initial association with the surface of the substrate through ionic bonds and/or electrostatic interaction. Preferably, the treated surface becomes permanently coated with a covalently bound octadecylammonium ion providing a durable, long-acting antimicrobial coating that is able to destroy microbes that come into contact with the surface.

Unfortunately, as noted above, organosilanes in water, such as the activated mixture of 3-(trimethoxysilyl)propyl-dimethyloctadecyl ammonium chloride and water are generally unstable and prone to self-condensation. For instance, the mixture of 3-(trimethoxysilylpropyl-dimethyloctadecyl ammonium chloride and water begins to lose effectiveness in as little as four to eight hours. Gel formation in this and similar silane formulations in water begins to occur in even shorter times. The limitations of such organosilanes in aqueous media are further described in U.S. Pat. No. 5,411,585, the contents of which are hereby incorporated by this reference. Moreover, such products are notorious for agitation difficulty during the addition of the silane to water. A limited list of additives useful for stabilizing organosilanes in water are described in U.S. Pat. Nos. 5,954,069; 6,113,815; 6,469,120; and 6,762,172.

The use of quaternary ammonium silicon compounds as antimicrobial agents in accordance with the prior art is well known and taught in a wide variety of United States patents, for example, U.S. Pat. Nos. 3,560,385; 3,794,736; and 3,814,739; the contents of which are hereby incorporated by reference. It is also taught that these compounds possess certain antimicrobial properties that make them valuable and very useful for a variety of surfaces, substrates, instruments, and applications (see, for example, U.S. Pat. Nos. 3,730,701; 3,794,736; 3,860,709; 4,282,366; 4,504,541; 4,615,937; 4,692,374; 4,408,996; and 4,414,268; the contents of which are hereby incorporated by reference). While these quaternary ammonium silicon compounds have been employed to sterilize or disinfect many surfaces, their employment is still limited because of their toxicity often as a result of the solvent system used to deliver the compound, the necessity for a solvent solution (for instance, Dow Corning antimicrobial agents contain 50% methanol), short term stability (stability of aqueous silane solutions varies from hours to several weeks only), and poor water solubility. For instance, while 3-(trimethoxysilyl)propyl-dimethyloctadecyl ammonium chloride does not suffer from water insolubility, it is difficult to dissolve in water and tends to form lumps before it slowly dissolves. It is unstable in water, and, because it is shipped in 50% methanol, it is overly toxic and flammable. Many other antimicrobial organosilanes, especially quaternary ammonium silicon compounds, also suffer from problems associated with physical health hazards—precautions must be taken to avoid contact with both skin and eyes, accidental spills to the surrounding area, flammability, and the added manufacturing steps needed in order to incorporate such antimicrobial agents into other articles and surfaces, resulting in much higher manufacturing costs.

Therefore, there exists a need for extended shelf-life, water-stable organosilane compounds, products, and compositions whereby, upon application, the active portion of the organosilane is operative for the selected application. Moreover, there exists a need for water-stable, organosilane compounds, products, and compositions that are essentially non-toxic, non-flammable, uniformly dispersible, and simple and economical to use. There also exists a need for highly concentrated organosilane compositions that are essentially non-toxic or of low toxicity, non-flammable, uniformly dispersible, simple and economical to use, and stable in water when further diluted with water.

BRIEF SUMMARY OF THE INVENTION

The present invention fulfills these needs by providing water-stable organosilane compounds, products, and compositions, methods for their use, and articles prepared using the compounds, products, and compositions. Advantageously, these compounds, products, and compositions are not oil-in-water emulsions.

In particular, the present invention provides the product formed from mixing an organosilane of the formula $R_nSiX_{4-n}$, where n is an integer from 0 to 3, preferably 0 to 2; each R is, independently, a non-hydrolyzable organic group; and each X is, independently, a hydrolyzable group (hereinafter, "organosilane of interest"); with an acidic stabilizing solution comprising at least one acid, at least one glycol ether, and at least one cationic surfactant in water. Although a combination of more than one acid, and/or more than one glycol ether, and/or more than one cationic surfactant can be used, it is preferred that the acidic stabilizing solution comprise one of each type of constituent. Preferably, the acid is an inorganic acid. More preferably, the acid is a mineral acid. Most preferably, the acid is hydrochloric acid. Preferably, the glycol ether is diethylene glycol butyl ether (CAS #112-34-5). Preferably, the cationic surfactant is a quaternary ammonium salt (QAS); preferably a dialkyl quat, a dialkyl/alkyl benzyl quat, or dialkyl dimethyl quat or similar quaternary surfactants, more preferably, an N-alkyl-N,N-Dimethyl-N-Benzyl ammonium chloride (CAS #68424-85-1). The resulting composition is between about 0.01% and about 49.99% water-stable antimicrobial organosilane compounds.

Generally, QAS take the form of structure I:

wherein each of $R^{38}$, $R^{39}$, $R^{40}$, and $R^{41}$ are independently selected from the group consisting of alkyl, aryl, and aralkyl, or the nitrogen may be part of a ring system; and X is an anion.

In a specific embodiment, $R^{38}=R^{39}=R^{40}=R^{41}$. In yet another embodiment, three of the four R substituents are selected from the same substituent. In yet another embodiment, two of the four R substituents are selected from the same substituent; the remainder of the substituents are either different from each other or the same as each other. In yet another embodiment, each R substituent is different.

Exemplary quaternary ammonium salts include, for example, (1-methyldodecyl)-trimethylammonium bromide, N-alkyl-N,N-dimethyl-N-benzyl ammonium chloride, trimethyl tallow ammonium chloride, polyquaternary ammonium chloride, and tetra-methylammonium bromide. The preferred QAS is N-alkyl-N,N-dimethyl-N-benzyl ammonium chloride.

The glycol ethers useful for the present invention are organic solvents having at least one ether moiety in a polymer chain and either a hydroxyl or alkoxy functional group. Preferably, the glycol ether is diethylene glycol butyl ether.

Accordingly, in one embodiment, this invention provides a water-stable composition comprising the product or composition of the invention and water.

In a further embodiment, the present invention provides a composition for treating a substrate, the composition comprising a carrier and an effective amount of the product or compound of the invention.

In yet another embodiment, the present invention provides methods of treating at least one substrate, the methods comprising mixing the substrate with a sufficient amount of the product, compound, or composition of the invention for a period of time sufficient for treatment of the substrate.

In a further embodiment, the present invention provides a composition for treating a substrate by incorporation into the substrate.

In a further embodiment, the present invention provides a composition as a concentrated solution, easily diluted with water, thereby providing a water stable composition.

In a further embodiment, the present invention provides an application to a concentrated solution, if not easily dissolved in water after aging, by applying an amine oxide or similar surfactant (for example and without limitation, (1-methyldodecyl)dimethylamine oxide and trimethylamine oxide) to the water prior or after silane addition to accelerate dissolution.

In a further embodiment, the present invention provides a composition as a concentrated solution to improve ease of dissolution in water, by applying an amine oxide or similar surfactant (for example and without limitation, (1-methyldodecyl)dimethylamine oxide and trimethylamine oxide) to the concentrate, to accelerate dissolution.

In a further embodiment, the present invention provides a composition as a concentrated solution that when diluted with water provides a white mixture easily clarified with acid or amine oxide or similar surfactant (for example and without limitation, (1-methyldodecyl)dimethylamine oxide and trimethylamine oxide).

In a further embodiment, the present invention provides a treated substrate having adhered thereto or dispersed therein the product, compound, or composition of the invention.

In addition, the present invention provides methods of dyeing and treating a substrate, wherein the methods comprise contacting the substrate with an aqueous composition comprising an aqueous soluble dye suitable for dyeing a substrate and the product formed from mixing an organosilane of interest with the acidified stabilizing solution.

A further embodiment of the present invention provides methods of antimicrobially treating at least one substrate selected the group consisting of a concrete pipe, a tooth brush, a food article, fluid container, latex medical article, gloves, shoes, a comb, a hair brush, a denture, an orthodontic retainer, a spa or pool filter, an air filter, an HVAC air system, a cabin air system, a marble article, a statue, an exposed work of art, an HDP plastic cover, a silicone or TEFLON® coated fiberglass article, a Dryvitt finish, a stucco finish, blended cotton, a bio-film, a bio-adhesive, a single ply roofing, a roofing shingle, and a fiberglass reinforcement product, comprising contacting the substrate with an effective amount of the product formed from mixing an antimicrobial organosilane of interest with the acidified stabilizing solution.

Another aspect of the present invention relates to methods of preparing the products, compounds, and compositions of the present invention. The preferred mixing sequence includes first adding at least one quaternary ammonium salt, at least one glycol ether, and water together and acidifying the solution, preferably to a pH between about 2 and about 3 to form an acidic stabilizing solution. Preferably, the at least one QAS comprises about 0.1 wt % to about 5 wt % of the stabilizing solution, and the at least an glycol ether comprises about 5 wt % to about 20 wt % of the solution. The preferred acid, HCl, is added to the aqueous solution in a sufficient quantity to lower the pH to any pH between about 2 and about 3. In some embodiments, a sufficient quantity of a base is added to increase the pH if too much acid is initially added. The balance of the solution may be water, preferably de-ionized water. The next step is adding the acidified stabilizing solution to the antimicrobial organosilane, preferably 3-(trimethoxysilyl)propyl-dimethyloctadecyl ammonium chloride. Surprisingly, adding the components of the stabilizing solution to the antimicrobial organosilane without first combining them in a solution and acidifying said solution results in a polymerized composition, wherein the antimicrobial organosilane self-condenses.

In addition, the present invention also provides methods of antimicrobially enhancing a product comprising admixing with rubbing alcohol, a flower preservative, or a waterproofing solution, an effective amount of the product formed from mixing an antimicrobial organosilane of interest with the acidified stabilizing solution.

A further embodiment of this invention is a method for making an organosilane of interest from starting materials in an aqueous solution in the presence of the acidified stabilizing solution.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DISCLOSURE OF THE INVENTION

The present invention may be understood more readily by reference to the following detailed description of preferred embodiments of the invention.

Before the present compounds, products, compositions, and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, where publications are referenced, the disclosures of these publications in their entireties are hereby incorporated by reference into this application.

The term "alkyl" as used herein refers to a branched or unbranched saturated hydrocarbon group of 1 to 24 carbon atoms, such as methyl ("Me"), ethyl ("Et"), n-propyl, isopropyl, n-butyl, isobutyl, t-butyl, octyl, decyl, tetradecyl, hexadecyl, eicosyl, tetracosyl, and the like. The term "cycloalkyl" intends a cyclic alkyl group from three to eight, preferably five or six carbon atoms. "Alkyl alcohol" refers to alkyl having attached thereto one or more hydroxy moieties, such as, but not limited to, —$CH_2CH_2OH$, $CH_2CH(OH)CH_3$, $CH_2OH$, $CH_2CH_2CH_2OH$, $CH_2CH_2CH(OH)CH_3$, $CH_2CH_2CH(OH)CH_2OH$, or $CH_2CH(OH)CH(OH)CH_3$. The term "small chain alkyl" refers to methyl, ethyl, propyl, and butyl.

The term "alkoxy" as used herein intends an alkyl group bound through a single terminal ether linkage; that is, an "alkoxy" group maybe defined as —OR where R is alkyl as defined above. "Polyether" refers to a compound or moiety possessing multiple ether linkages, such as, but not limited to, polyethylene glycols or polypropylene glycols. "Polyalkylethers" refers to alkyls interconnected by or otherwise possessing multiple ether linkages.

As used herein, "optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyls and lower alkyls where there is substitution.

By the term "effective amount" of a compound, product, or composition as provided herein is meant a sufficient amount of the compound, product, or composition to provide the desired result. As will be pointed out below, the exact amount required will vary from substrate to substrate, depending on the particular compound, product, or composition used, its mode of administration, and the like. Thus, it is not always practical to specify an exact "effective amount," especially because arrange of amounts or concentrations will usually be effective. However, an appropriate effective amount may be determined by one of ordinary skill in the art using only routine experimentation as a matter of optimization.

The term "aryl" as used herein refers to a compound or moiety whose molecules have a ring or multiple ring structure characteristic of benzene, naphthalene, phenanthrene, anthracene, etc., such as, either the six-carbon ring of benzene or the condensed six-carbon rings of the other aromatic derivatives, including, but not limited to phenyl, benzyl, naphthyl, benzylidine, xylil, styrene, styryl, phenethyl, phenylene, benzenetriyl, etc.

As used herein, the term "aromatic" refers to the group of unsaturated cyclic hydrocarbons, typified by benzene, having a 6-carbon ring containing three double bonds or multiple attached benzene rings. Moreover, certain five membered cyclic compounds, such as furan (heterocyclic), are analogous to aromatic compounds. Aromatics include the cyclic compounds based upon a benzene functionality, as specified for "aryl" above.

Moreover, the term "cyclic" is used to refer to all aliphatic or aromatic hydrocarbons having one or more closed rings, whether unsaturated or saturated. Preferably, cyclic compounds possess rings from 5 to 7 carbon atoms, preferably 6 carbon atoms. Such rings fall into three classes: alicyclic, aromatic ("arene"), and heterocyclic. Moreover, when used with respect to cyclic compounds or moieties, the term "unsaturated" refers to such compound or moiety possessing at least one double or triple bond or otherwise constituting an aromatic compound or moiety. Moreover, the term "saturated" refers to compounds or moieties possessing no double or triple bonds, that is, where all available valence bonds of an atom, especially carbon, are attached to other atoms.

The term "heteroaryl" refers to an aryl where one or more of the carbon atoms of a ring have been substituted with a heteroatom, including, but not limited to, O, N, or S.

Similarly, the term "heterocyclic" refers to a cyclic compound or moiety where one or more of the carbon atoms of the ring have been substituted with a heteroatom, including, but not limited to O, N, or S.

As used herein, especially in reference to alkyl and alkoxy, the term "lower" refers to a moiety having from 1 to 6 carbon atoms, preferably 1 to 4 carbon atoms.

As used herein, the term "suitable" is used to refer to a moiety that is compatible with the compounds, products, or compositions as provided herein for the stated purpose. Suitability for the stated purpose may be determined by one of ordinary skill in the art using only routine experimentation.

As used herein, "substituted" is used to refer, generally, to a carbon or suitable heteroatom having a hydrogen or other atom removed and replaced with a further moiety. In one embodiment, halogen, hydroxy, and nitrogen-based substitutions of hydrocarbon hydrogens are contemplated as within the scope of the present invention for the claimed structures. Moreover, it is intended that "substituted" refer to substitutions which do not change the basic and novel utility of the underlying compounds, products, or compositions of the present invention.

"Unsubstituted" refers to a structure wherein the reference atom does not have any further moieties attached thereto or substituted therefor.

As used herein, "branched" is used to refer, generally, to a moiety having a carbon chain backbone, for example, alkyl or alkoxy, wherein the backbone may contain one or more subordinate carbon chain branches. For example, isobutyl, t-butyl, isopropyl, $CH_2CH_2C(CH_3)(H)CH_2CH_3$, $CH_2C(CH_2CH_3)(H)CH_2CH_3$, $CH_2CH_2C(CH_3)CH_3$, and $CH_2CH_2C(CH_3)_3$ would all be considered branched moieties. Moreover, it is intended that "branched" variations of the moieties herein described refer to variations that do not change the basic and novel utility of the underlying compounds, products, or compositions of the present invention. "Unbranched" refers to a structure wherein the carbon chain does not have any branches thereon, that is, where the carbon chain extends in a direct line.

As used herein, the term "acyl" refers to organic acid derived moieties of the formula RCOX where R is an organic molecule and X, instead of being hydroxy, is replaced with another substituent, preferably a suitable anion, such as a halogen including, but not limited to, F, Cl, Br, or L.

As used herein, the term "perfluoro" or "perfluoro-analog" refers to a hydrocarbon where the hydrogen atoms attached to carbons have been replaced with F atoms. Preferably, but not necessarily, in perfluoro-analogs, most, if not all, of the H atoms are replaced with F atoms. A "fluoro-" analog is contemplated to indicate a hydrocarbon where at least one hydrogen atom attached to a carbon is replaced with an F atom.

As used herein, the term "product" or "products" generally refers to the compounds or compositions formed from performing a specified reaction; and also encompasses the result of mixing, combining, or reacting more than one compound or composition.

As used herein, "substrate" refers to any article, product, or surface that can be treated with the inventive compounds, preferably as enumerated hereinbelow under the heading "Uses," as described in the Examples hereto, and as specified in the relevant claims appended hereto. Suitable substrates are generally characterized by either having a negatively charged surface of oxygen atoms, or any surface capable of electrostatically, ionically, or covalently adhering or binding to the compounds, products, or compositions of the present invention. Preferably the adhering or binding occurs at the silicon atoms of the organosilane portion of the compounds, products, or compositions of the present invention, but such binding is not a requirement. "Substrate" also refers to materials that are treated by incorporation of the compounds and/or compositions of the present invention. Incorporation in this case includes the process of blending and mixing, and incorporation by becoming part of the material, for example, polymer backbone and cement. Therefore, as used herein, the term "adhere" is meant to refer to ionic, covalent, electrostatic, or other chemical attachment of a compound, product, or composition to a substrate.

As used herein, the term "antimicrobially enhancing" refers to the use of the compounds, products, or compositions of the present invention, preferably those wherein the organosilane has antimicrobial activity along with other ingredients, surfactants, fillers, wetting agents, pigments, dyes, antimigrants, etc., to create a composition or solution capable of fulfilling its original purpose, based upon the other ingredients, and also of providing antimicrobial protection during the particular application.

The term "enhance" refers to the addition of antimicrobial activity to such compositions or solutions where no such activity previously existed, or to the increase of antimicrobial activity where the starting compositions or solutions already possessed antimicrobial activity.

As used herein, "hydrolyzable" refers to whether the moiety is capable of or prone to hydrolysis (for example, splitting of the molecule or moiety into two or more new molecules or moieties) in aqueous or other suitable media. Conversely, "non-hydrolyzable" refers to moieties that are not prone to or capable of hydrolysis in aqueous or other suitable media.

As used herein, "cationic" is used to refer to any compound, ion, or moiety possessing a positive charge. Moreover, "anionic" is used to refer to any compound, ion, or moiety possessing a negative charge. Furthermore, "monovalent" and "divalent" are used to refer to moieties having valances of one and two, respectively.

As used herein, the term "salt" is meant to apply in its generally defined sense as "compound formed by replacing all or part of the hydrogen ions of an acid with one or more cations of a base." See, for example, American Heritage Dictionary, Definition of "Salt" (1981). Therefore, suitable salts for the present invention may be formed by replacing a hydrogen ion of a moiety with a cation, such as $K^+$, $Na^+$, $Ca^{2+}$, $Mg^{2+}$, etc. In addition, other suitable methods of generating salts are specified throughout this specification and are within the scope of the present definition. For the purposes of the present invention, the specific identity of the cation used for forming the salt is of lesser importance than the chemical structure of the anion of which the salt is formed.

As used herein, "food article" refers to perishable or non-perishable foods such as meats, fruits and vegetables and other foods such as grains and dairy products. In preferable embodiments, the food articles referred to herein are those that are perishable or prone to spoilage upon exposure to microbes or other pathogens. In addition, a "consumable product" is meant to refer to food articles, fluids for drinking, medicines for ingestion, or any other product introduced internally via any means into a human or animal.

As used herein, the term "antimicrobial" is used in its general sense to refer to the property of the described compound, product, composition, or article to prevent or reduce the growth, spread, formation, or other livelihood of organisms such as bacteria, viruses, protozoa, molds, or other organisms likely to cause spoilage or infection.

As used herein, the term "medical article" is used to refer to any suitable substrate that is or may come into contact with medical patients (human or animal), medical caregivers, bodily fluids, or any other source of contamination or infection generally associated with hospitals, clinics, physician's offices, etc.

As used herein, the terms "quaternary ammonium salt" or "quaternary ammonium salts" refer to salts of quaternary ammonium cations with an anion and are interchangeable with the acronym "QAS" or "quat".

The terms "comprising", "consisting of", and "consisting essentially of" are defined according to their standard meaning and may be substituted for one another throughout the instant application in order to attach the specific meaning associated with each term.

As used in this specification and the appended claims, the singular forms "a", "an", and "the" include plural reference unless the context clearly dictates otherwise. Thus, for example, a reference to "a composition" includes more than one such composition, a reference to "the substrate" includes more than one such substrate, and the like.

The present invention provides water-stabilized and solubilized organosilane compounds, products, and compositions, methods of their use, and articles prepared using the compounds, products, and compositions. In particular, the present invention is useful in stabilizing a broad variety of organosilanes of the general formula $R_nSiX_{4-n}$ where n is an integer from 0 to 3, preferably 0 to 2; R is a non-hydrolyzable organic group, such as but not limited to, alkyl, aromatic, organofunctional, or a combination thereof; and X is halogen, such as but not limited to, Cl, Br, or I, or N is hydroxy, alkoxy such as methoxy or ethoxy, acetoxy, or unsubstituted or substituted acyl. For such organosilanes, X is prone to react with various hydroxyl containing molecules.

Alternatively, where the stabilizers are not sufficiently water-soluble, additional stability is achieved by mixing the organosilane with the stabilizer in a non-aqueous solvent. In such an alternative preparation, the remaining solvent (for example, methanol) is liberated via distillation, freeze-drying, evaporation or other methods known in the art for removal of volatile organic solvents.

The solutions are stable for extended periods, for example, from several days to several months. It will also be recognized that while aqueous silane stock solutions of up to 50% silane may be stabilized by the acidified stabilizing solution disclosed herein, working silane concentrations tend to be in the 0.001-15% silane range where the stabilization effects of the herein disclosed stabilizers are less challenged by the higher silane concentrations required in stock solutions The solutions of the present invention are, in certain preferred embodiments, useful for the application of various organosilane coupling agents to surfaces in industrial and household uses without the use of toxic and/or flammable organic solvents. One of ordinary skill in the art would recognize that the preparation steps are merely guidelines and such a person would, without undue experimentation, be able to prepare the composition by varying the parameters for contacting or mixing the organosilane of interest and the acidified stabilizing solution and order of introduction of reagents and starting materials without deviating from the basic and novel characteristics of the present invention.

Products

With the aforementioned definitions in mind, the present invention provides the product formed from mixing an organosilane of the formula $R_nSiX_{4-n}$ where n is an integer from 0 to 3, preferably 0 to 2; each R is, independently, a non-hydrolyzable organic group; and each X is, independently, a hydrolyzable group and an acidic stabilizing solution comprising at least one acid, at least one glycol ether, and at least one cationic surfactant in water. Preferably, the acid is an inorganic acid. More preferably, the acid is a mineral acid. Most preferably, the acid is hydrochloric acid. Preferably, the glycol ether is diethylene glycol butyl ether (CAS #112-34-5). Preferably, the cationic surfactant is a quaternary ammonium salt; preferably a dialkyl quat, a dialkyl/alkyl benzyl quat, or dialkyl dimethyl quat or similar quaternary surfactants, more preferably an N-alkyl-N,N-Dimethyl-N-Benzyl ammonium chloride (CAS #68424-85-1). Preferably, the pH of the acidic stabilizing solution is between about 2 and about 3. More preferably, the pH is about 2.5.

Generally, QAS take the form of structure 1:

(I)

wherein each of $R^{38}$, $R^{39}$, $R^{40}$, and $R^{41}$ are independently selected from the group consisting of alkyl, aryl, and aralkyl, or the nitrogen may be part of a ring system; and X is an anion.

Preferably, at least one of $R^{38}$, $R^{39}$, $R^{40}$, or $R^{41}$ is an alkyl. More preferably, the alkyl substituent has a $C_6$ to $C_{18}$ hydrocarbon chain. Most preferably, the alkyl substituent has a $C_{12}$ to $C_{16}$ hydrocarbon chain. In yet another embodiment, at least one of $R^{38}$, $R^{39}$, $R^{40}$, or $R^{41}$ is a methyl substituent. In yet another embodiment, at least one of $R^{38}$, $R^{39}$, $R^{40}$, or $R^{41}$ is a methyl substituent, and at least one of $R^{38}$, $R^{39}$, $R^{40}$, or $R^{41}$ is an alkyl having a $C_6$ to $C_{18}$ hydrocarbon chain.

In a specific embodiment, $R^{38}=R^{39}=R^{40}=R^{41}$. In yet another embodiment, three of the four R substituents are selected from the same substituent. In yet another embodiment, two of the four R substituents are selected from the same substituent; the remainder of the substituents are either different from each other or the same as each other. In yet another embodiment, each R substituent is different.

Exemplary quaternary ammonium salts include, for example and without limitation, (1-methyldodecyl)-trimethylammonium bromide, N-alkyl($C_{12}$-$C_{16}$)-N,N-dimethyl-N-benzyl ammonium chloride, trimethyl tallow ammonium chloride, poylquaternary ammonium chloride, tetra-methylammonium bromide, benzyl tributyl ammonium chloride, benzyl triethyl ammonium bromide, benzyl trimethyl ammonium chloride, cetyl pyridinium bromide, cetyl pyridinium chloride, cetyl trimethyl ammonium bromide, didecyl dimethyl ammonium chloride, dimethyl distearyl ammonium bisulfate, dimethyl distearyl ammonium methosulfate, dodecyl trimethyl ammonium bromide, dodecyl trimethyl ammonium chloride, methyl tributyl ammonium chloride, methyl tributyl ammonium hydr. sulfate, methyl tricaprylyl ammonium chloride, methyl trioctyl ammonium chloride, myristyl trimethyl ammonium bromide, phenyl trimethyl ammonium chloride, tetrabutyl ammonium. borohydride, tetrabutyl ammonium bromide, tetrabutyl ammonium chloride, tetrabutyl ammonium fluoride, tetrabutyl ammonium hydrogen sulfate, tetrabutyl ammonium hydroxide, tetrabutyl ammonium iodide, tetrabutyl ammonium perchlorate, tetraethyl ammonium bromide, tetraethyl ammonium chloride, tetraethyl ammonium hydroxide, tetrahexyl ammonium bromide, tetrahexyl ammonium iodide, tetramethyl ammonium bromide, tetramethyl ammonium chloride, tetramethyl ammonium fluoride, tetramethyl ammonium hydroxide, tetramethyl ammonium iodide, tetraoctyl ammonium bromide, tetrapropyl ammonium bromide, tetrapropyl ammonium chloride, tetrapropyl ammonium hydroxide, tributyl methyl ammonium chloride, triethyl benzyl ammonium chloride, N-alkyl (60% $C_{14}$, 30% $C_{16}$, 5% $C_{12}$, 5% $C_{18}$) dimethyl benzyl ammonium chloride, N-alkyl(68% $C_{62}$, 32% $C_{14}$) dimethyl ethylbenzyl ammonium chloride.

Preferably, the acid utilized to acidify the stabilizing solution is an inorganic acid. More preferably, the acid is a mineral acid. Most preferably, the acid is hydrochloric acid.

In another specific embodiment, the acid is an organic acid, preferably acetic acid.

However, the present invention encompasses acids including, for example and without limitation, acetic, adipic, anisic, arsenic, arsenious, benzoic, boric, bromic, bromous, butanoic, capric, caproic, caprylic, carbonic, chloric, chlorous, chromic, chromous, cinnamic, citric, cyanic, cyanoacetic, diphosphonic, disulfuric, disulfurous, dithionic, dithionous, ferricyanic, ferrocyanic, fluorosilicic, formic, fulminic, fumaric, gallic, glutaric, glycolic, hexadecanoic, hexafluorosilicic, hydrobromic, hydrochloric, hydrocyanic, hydrofluoric, hydroiodic, hydroxybenzoic, hypochlorous, iodic, iodous, isocyanic, isothiocyanic, lactic, lauric, levulinic, maleic, malic, malonic, manganic, molybdic, nitric, nitrous, octadecanoic, oleic, oxalic, pentanoic, valeric, perchloric, periodic, pertechnetic, phosphinic, phosphonic, phosphoric, phthalic, picric, propanoic, pyrogallic, pyruvic, rhenic, salicylic, selenic, selenious, silicic, stearic, succinic, sulfanilic, sulfuric, sulfurous, tartaric, telluric, tellurous, thioacetic, thiocyanic thiosulfurous, titanic, tungstic, uranic, valeric, and vanillic acids.

Preferably, the concentration of the acid is about 1 $\underline{M}$.

Moreover, a sufficient amount of acid is added to the stabilizing solution to reduce the acidity to a pH level within the range of about 2 to about 3. In one specific embodiment, the pH is about 2. In yet another specific embodiment, the pH is about 2.5. In yet another specific embodiment, the pH is about 3. Although previous organosilane compositions have been known to be water-stable at unknown pHs (U.S. Pat. No. 6,762,172), surprisingly, the present invention's compositions were unexpectedly found to be water-stable for at least several days when the pH was reduced to a level between about 2 and about 3. Preferably, the pH of the compositions and products of the present invention is about 2.5. There has never been a teaching about this particular pH effect on the stability of aqueous organosilane compositions.

The present invention also contemplates adding a sufficient amount of a base to adjust the pH to the desired target pH. Preferably, the base is NaOH.

Although previous organosilanes have been stabilized with polyols that possibly contain an ether group (U.S. Pat. Nos. 5,959,014; 6,221,944; and 6,632,805), the glycol ethers used in the present invention are not polyols. The glycol ethers utilized in the present invention do not have multiple hydroxyl moieties (that is, more than three) as suggested in the aforementioned patents nor are the hydroxyl and ether moieties required to be spaced apart by a minimum number of elements. Moreover, an acidic stabilizing solution prepared from only a glycol ether and water is unlikely to prevent self-condensation of the organosilane of interest. It is the combination of both the at least one QAS and the glycol ether in an aqueous, acidic solution that provides the requisite stability to the antimicrobial organosilane. The preferred glycol ether utilized in the present invention is diethylene glycol butyl ether. Advantageously, the addition of a glycol ether improves the wetting and dispersion properties of the present invention. The components disperse in water quickly with a minimum of physical mixing of agitation.

Exemplary glycol ethers useful in the present invention include, but are not limited to:
ethylene glycol monobutyl ether,
ethylene glycol monoethyl ether,
ethylene glycol monobutyl ether acetate,
diethylene glycol monobutyl ether acetate,
diethylene glycol monoethyl ether,
propylene glycol n-butyl ether (DB),
propylene glycol methyl ether (PM),
propylene glycol methyl ether acetate (PMA),
ethylene glycol butyl ether (EB),
triethylene glycol monomethyl ether,
triethylene glycol monoethyl ether,
triethylene glycol monobutyl ether,
ethylene glycol phenyl ether,
diethylene glycol n-butyl ether acetate,
diethylene glycol monobutyl ether,
ethylene glycol n-butyl ether acetate,
hydroxy-polyether,
diethylene glycol monohexyl ether,
ethylene glycol monohexyl ether,
diethylene glycol monomethyl ether,
ethylene glycol n-propyl ether,
dipropylene glycol methyl ether,
dipropylene glycol methyl ether acetate,
dipropylene glycol n-butyl ether,
dipropylene glycol n-propyl ether,
propylene glycol n-butyl ether,
propylene glycol n-propyl ether,
propylene glycol phenyl ether,
tripropylene glycol methyl ether,
tripropylene glycol n-butyl ether, and
dipropylene glycol dimethyl ether.

Advantageously, the present invention is stable following freezing and thawing. Previous organosilane compositions have polymerized during and immediately after thawing from a frozen state. Surprisingly, the present invention is able to withstand multiple cycles of freezing and thawing without destabilizing by polymerization. Without being limited by theory, it is believed that the acidic stabilizing solution protects the silane moieties of the organosilane ingredient from being punctured by water crystals that may form during freezing. The advantageous ability of the present invention to undergo freeze and thaw cycles without polymerization is particularly desirable when the invention is transported or stored in cold environments.

More preferably, in the product prepared from mixing an organosilane of the formula:

$$R_nSiX_{4-n}$$

with the aforementioned acidic stabilizing solution, n is an integer from 0 to 2, preferably 1; each R is, independently, alkyl, preferably from 1 to 22 carbon atoms branched or unbranched, substituted or unsubstituted, more preferably from 1 to 6 carbon atoms, or from 10 to 20 carbon atoms, most preferably from 1 to 4 carbon atoms or from 14 to 18 carbon atoms; alkyl alcohol of similar carbon lengths, branching, and substitution, or aromatic, such as benzyl, phenyl, etc.; each X is, independently, hydroxy, alkoxy, halogen (such as, but not limited to, Cl, Br, I, or F), acetyl, acetoxy, acyl, a hydroxylated solid or liquid polymeric moiety, polyether or polyalkylether.

Each, independently, in a weight-ratio from 0 to 100%, substituted by R' in a number from 0 to the number of replaceable hydroxide hydrogen; and with R' in place of either hydroxyl hydrogen or hydroxyl group, being independently H, alkyl from 1 to 24 carbon atoms, carbonic acid from 1 to 24 carbon atoms, R" ring substituted aromatic phenol, heteroaryl ring substituted with R", phenol, $(R''—)_x$ ring substituted saturated or unsaturated cyclic alcohol, where x is an integer from 0 to 15. The cycle or ring size is from 3 to 8 carbon atoms, for the heterocycles O, N, and S are replacing carbon atoms in any number and combination; where R''' is H, F, Cl, Br, I, CN, SCN, $NH_2$, alkyl from 1 to about 24 carbon atoms, acetyl, acetoxy, acyl, or $X_2PO_4$, where X is any suitable cation.

In addition R can contain a $R'''_xY_{3-x}PO_4$ group with x being an integer of 1 to 3 and R''' equals R, R as described above with the limitation that each R contains not more than 4 $R'''_xY_{3-x}PO_4$ groups.

In a further embodiment of the invention, the invention provides the product described above, wherein the organosilane is of the formula I, II, III, or IV

  (I)

  (II)

  (III)

  (IV)

wherein each $R^1$ is, independently, halogen or $R^6O$;

where $R^6$ is H, alkyl from 1 to about 24 carbon atoms, acetyl, acetoxy, acyl, propylene glycol, ethylene glycol, polyethylene glycol, polypropylene glycol; block and copolymers of ethylene and propylene glycol, the alkyl monoether from 1 to 24 carbons of propylene glycol, ethylene glycol, polyethylene glycol, polypropylene glycol; block and copolymers of ethylene and propylene glycol or the monoester of a carbonic acid from 1 to 24 carbons and propylene glycol, ethylene glycol, polyethylene glycol, polypropylene glycol; block and copolymers of ethylene and propylene glycol; octylphenol, nonylphenol, and sorbitan ethers;

$R^{35}$ is $R^6$, H, halogen (such as Cl, Br, F, or I), $NH_2(CH_2)_2NHR^2NH_2R^2$, $C_3H_5O_2R^2$, $C_4H_5O_2R^2$, NaO$(CH_3O)P(O)R^2$, or $ClCH_2C_6H_4R^2$;

$R^{36}$ and $R^{37}$ are, independently, $R^{35}$, halogen, H, alkyl, preferably from 1 to 4 carbon atoms, more preferably from 1 to 2 carbon atoms, isobutyl, phenyl, or n-octyl;

$R^2$ is $R^6$, benzyl, vinyl or alkyl;

$R^3$ and $R^4$ are, independently, $R^{35}$, alkyl alcohol, alkoxy, alkyl from 1 to 24 carbon atoms, preferably 1 to about 10 carbon atoms, more preferably alkyl from 1 to 4 carbon atoms, or more preferably from 1 to 2 carbon atoms;

$R^3$ and $R^4$ can, together, form a morpholine or cyclic or heterocyclic, unsaturated or saturated, five to seven-membered ring of the formula V:

  (V)

where k is an integer from 0 to 2, preferably 0 to 1, most preferably 1;

$R^7$, where the ring is saturated is $CH_2$, O, S, NH, $NH_2^+$, $NCH_2CH_2NH_2$, $NCH_3^+$, $NCH_2CH_2N(R^8)(R^9)$, $NCH_2CH_2N^+(R^8)(R^9)(R^{10})$, N(alkyl), N(aryl), N(benzyl), where each $R_8$, $R^9$, and $R^{10}$ is, independently, benzyl, $R^{37}$, polyether, preferably from 1 to 4 carbon atoms, alkyl alcohol, preferably from 1 to 4 carbon atoms, alkoxy, preferably from 1 to 4 carbon atoms, or alkyl, from 1 to 24 carbon atoms, preferably 1 to about 10 carbon atoms, and the "alkyl" specified above is from 1 to 24 carbon atoms, more preferably from 1 to 10 carbon atoms, most preferably from 1 to 3 carbon atoms, the "aryl" is more preferably phenyl or benzyl, and $R^7$, where the ring is unsaturated is CH, N, $N^+H$, $N^+$(alkyl), $N^+$(aryl), $N^+$(benzyl), $N—CH_2—N$, $N^+H—CH_2—N$, $N^+$(alkyl)$-CH_2—N$, $N^+$(aryl)$-CH_2—N$, or $N^+$(benzyl)$-CH_2—N$, where the alkyl, aryl, or benzyl is as described above; wherein the ring is unsubstituted or substituted with alkyl from 1 to 24 carbon atoms, more preferably from 1 to 10 carbon atoms, most preferably from 1 to 3 carbon atoms, ester, aldehyde, carboxylate (preferably acetoxy, acetyl, acyl or perfluorocarboxylate) amide, thionamide, nitro, amine, or halide, most preferably Cl, Br, or I;

and the ring provided by formula V represents $R^3$ or $R^4$, independently, with the ring nitrogen of formula I or II replaced by CH or $CH_2$. This ring is attached to the nitrogen in structure I or II, by removing any one hydrogen from the structure and placing a bond from the nitrogen of I or II to the atom missing the hydrogen.

$R^5$ is alkyl alcohol, preferably from 1 to 6 carbon atoms, more preferably from 1 to 4 carbon atoms, $R^{35}$, $CH_2C_6H_5$, polyether, such as a polyethylene glycol or a polypropylene glycol, alkyl from 1 to 24 carbon atoms, preferably from 1 to 10 carbon atoms, most preferably from 1 to 6 carbon atoms, alkoxy, from 1 to 24 carbon atoms, more preferably from 1 to 10 carbon atoms, most preferably from 1 to 6 carbon atoms, perfluoroalkyl, from 1 to 24 carbon atoms, more preferably from 1 to 10 carbon atoms, most preferably from 1 to 6 carbon atoms, perfluoroalkylsulfonate, from 1 to 24 carbon atoms, more preferably from 1 to 10 carbon atoms, most preferably from 1 to 6 carbon atoms, perfluoroalkylcarboxylate, or is a five to seven-membered ring of formula V as described above; and $Y^-$ is a suitable anionic moiety to form the salt of the compound of formula I, II, III, or IV.

Compositions

This invention provides a water stable composition comprising water and an organosilane of interest mixed with an acidic stabilizing solution, and a composition providing silane and an acidic stabilizing solution, easily dissolved in many solvents, including water, that is advantageously storable and water stable when diluted with water. Optionally, the water stable composition further comprises an amine oxide surfactant or a nonionic surfactant, preferably alkylphenol ethoxylate. Furthermore, the present invention's compositions provide silane coatings that are capable of migration.

The present invention provides a composition for treating a substrate, wherein the composition comprises a carrier and an effective amount of an organosilane of interest and an acidified stabilizing solution as described herein. The carrier may be water, or in further embodiments, the carrier is other than water.

Moreover, the present invention also provides a composition resulting from mixing an organosilane of the formula I, II, III, or IV:

  (I)

  (II)

  (III)

  (IV)

as substantially previously described with reference to the formula numbers I, II, III, and IV, with an acidified stabilizing solution according to the invention as described above.

The weight percentage of the antimicrobial organosilane in the composition varies according to the target application, but generally, the antimicrobial organosilane of interest comprises about 0.1 wt % to about 50 wt % of the composition, Diluted compositions, which are useful for application to, for example, food stuffs, contain about 0.1 wt % to about 1 wt % of the antimicrobial organosilanes. In a specific embodiment, the organosilane can comprise about 0.2 wt %, 0.3 wt %, 0.4 wt %, 0.5 wt %, 0.6 wt %, 0.7 wt %, 0.8 wt %, and 0.9 wt %. In other applications, the antimicrobial organosilane comprises about 1 wt % to about 15 wt % of the composition. In a specific embodiment, the weight percentage of the organosilane of interest is within the range of about 3 wt % and 7.5 wt %. In yet another embodiment, the weight percentage is about 5 wt % to about 5.5 wt %. In yet another embodiment, the antimicrobial organosilane comprises about 15 wt % to about 35 wt % of the composition. Exemplary organosilane weight percentages are about 15 wt %, about 20 wt %, about 25 wt %, about 30 wt %, and about 35 wt %. In one embodiment, QAS comprises about 1 wt % to about 5 wt % of the present invention, are a glycol ether comprising about 17 wt % to about 23 wt %. In a preferred embodiment, the antimicrobial organosilane comprises about 15 wt % of the composition, the QAS comprises about 2 wt % of the composition, diethylene glycol butyl ether comprises about 20 wt % of the composition, and water comprises the balance of composition.

In a further embodiment, the balance of the composition is water, preferably de-ionized water.

Surprisingly, the present compositions, although not oil-in-water emulsions, remain stable and do not polymerize or precipitate for at least a week after preparation. Advantageously, when the present invention's compositions and products are prepared and stored for future usage, the non-emulsified compositions and products do not self-condense nor do solids precipitate out of solution.

Additionally, the compositions and products do not require a siliconate salt in order to stabilize the antimicrobial organosilane in water. (cf, U.S. Pat. No. 4,503,242). Surprisingly, as discussed in more detail above, the antimicrobial organosilane of interest remains water-stable for several days by the addition of the acidified stabilizing solution.

Methods

Another aspect of the present invention relates to methods of preparing the products, compounds, and compositions of the present invention. The mixing sequence includes first adding at least one quaternary ammonium salt, a glycol ether, and water together and acidifying the solution, preferably to a pH between about 2 and about 3. Preferably, the at least one QAS comprises about 0.1 wt % to about 5 wt % of the stabilizing solution and the glycol ether comprises about 5 wt % to about 20 wt % of the solution. The balance of the solution may be water, preferably de-ionized water. The order of the addition of the components to the stabilizing solution is unimportant except the acid should be added to the water. The next step is adding the acidified stabilizing solution to the antimicrobial organosilane, preferably 3-(trimethoxysilyl) propyl-dimethyloctadecyl ammonium chloride. Interestingly, adding the components of the stabilizing solution to the antimicrobial organosilane without first combining them in a solution and acidifying said solution results in a polymerized composition wherein the antimicrobial organosilane self-condenses.

In addition, the present invention also provides methods of treating at least one substrate, the methods comprising contacting each substrate with a sufficient amount of the composition as described above for a period of time sufficient for treatment of the at least one substrate. Moreover, in an alternate embodiment, the present invention provides methods of treating at least one substrate, the methods comprising contacting each substrate with a sufficient amount of the compound as described above for a period of time sufficient for treatment of each substrate.

In yet another embodiment, the present invention provides methods of dyeing and treating at least one substrate, the methods comprising contacting the substrate with an aqueous or substantially water soluble composition comprising an aqueous soluble dye suitable for dyeing a substrate and the product formed from mixing an organosilane of interest and an acidified stabilizing solution.

In yet another embodiment, the present invention provides methods of antimicrobially treating at least one substrate selected from the group consisting of a concrete pipe, food article, fluid container, glove, show, latex medical article, a tooth brush, a comb, a hair brush, a denture, an orthodontic retainer, a spa or pool filter, an air filter, an HVAC air system, a cabin air system, a marble article, a statue, an exposed work of art, an HDP plastic cover, a silicone or TEFLON® coated fiberglass article, a Dryvitt finish, a stucco finish, blended cotton, a bio-film, a bio-adhesive, a single ply roofing, a roofing shingle, and a fiberglass reinforcement product, wherein the methods comprise contacting the substrate with an effective amount of the product formed from mixing an antimicrobial organosilane of interest and an acidified stabilizing solution.

A further embodiment of the present invention provides methods of antimicrobially enhancing a product of rubbing alcohol, a flower preservative, or a waterproofing solution, the methods comprising admixing with the product an effective amount of the product formed from mixing an antimicrobial organosilane of interest with an acidified stabilizing solution.

Substrates

In addition, the present invention provides a treated substrate having adhered thereto the composition produced by contacting the organosilane and the acidified stabilizing solution as described above. Alternatively, the present invention provides a treated substrate having adhered thereto a compound produced by contacting the organosilane and the acidified stabilizing solution as described above.

Silanes

The present invention is useful for stabilizing antimicrobial organosilanes of the general formula:

$R_nSiX_{4-n}$ where n is an integer from 0 to 3, preferably 0 to 2;

R is a non-hydrolyzable organic group (alkyl, aromatic, organofunctional or a combination thereof); and X is hydroxy, alkoxy, preferably methoxy or ethoxy, halogen (preferably Cl, Br, or I), acetoxy, acyl, substituted acyl, or a hydrolyzable polymer or other moiety prone to hydrolysis and/or environmental harmfulness.

The organosilanes used in the practice of the present invention need not be, and often are not, water soluble. By varying the stabilizer and preparation method, the organosilanes selected for use in the present invention are solubilized in water by the stabilizer.

Numerous art-known organosilanes are suitable for the present stabilization procedures to produce water-stabilized compounds, products and compositions. U.S. Pat. Nos. 5,411,585; 5,064,613; 5,145,592, and the publication entitled "A Guide to DC Silane Coupling Agent" (Dow Corning, 1990) disclose many suitable organosilanes. The contents of these references are hereby incorporated in their entirety herein by this reference for the teachings of suitable organosilanes. These organosilanes are suitable for the formation of the water-stabilized organosilane compounds, products, and compositions of the present invention. In addition, the disclosure of U.S. Pat. No. 4,390,712 is hereby incorporated by reference for its teaching of siloxane synthesis in an aqueous medium. Per the instant disclosure, those skilled in the art will appreciate that the aqueous siloxane synthesis methods of the 4,390,712 patent are modified to advantage by performing the siloxane synthesis in the presence of the QAS stabilizer as defined herein, thereby forming a stabilized siloxane-water composition while still taking advantage of the accelerated kinetics of siloxane formation in aqueous media noted in the 4,390,712 patent. Accordingly, a further embodiment of this invention is a method for making an organosilane of the formula $R_nSiX_{4-n}$ where n is an integer from 0 to 3, preferably 0 to 2; each R is, independently, a non-hydrolyzable organic group; and each X is, independently, a hydrolyzable group; from starting materials in an aqueous solution in the presence of an effective amount of at least one QAS, sufficient to stabilize the organosilane as it is formed from the reactants.

Preferred silanes for use in the compounds, products and compositions and methods of the present invention include silanes of the following formula:

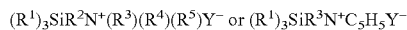

wherein each $R^1$ is, independently, halogen (Cl, Br, I, F) or $R^6O$, where $R^6$ is H, alkyl from 1 to about 6 carbon atoms, unsubstituted or substituted, preferably from 1 to about 2 carbon atoms and more preferably 1 carbon atom, or acetyl or other acyl, including substituted acyl; or $R^6O$ can be derived from any hydroxylated polymer, hydroxylated liquid, or hydroxylated solid regardless of water solubility; or $R^6O$ can be derived from any polyether such as, but not limited to, polyethyleneglycols or polypropyleneglycols, such as poly(propyleneglycol)triol (glycerol propoxylate);

$R^2$ is unsubstituted or substituted benzyl or an unsubstituted or substituted alkyl from 1 to about 3 carbon atoms, preferably alkyl from 1 to 3 carbon atoms;

$R^3$ and $R^4$ are, independently, lower alkoxy from 1 to 4 carbon atoms, preferably of 2 carbon atoms, such as $CH-,CH)OH$, $CH_2CH(OH)CH_3$, alkyl from 1 to about 22 carbon atoms, preferably from 1 to about 10 carbon atoms and most preferably from 1 to 2 carbon atoms or $R^3$ and $R^4$ can, together, form a morpholine or other cyclic or heterocyclic, unsaturated or saturated, five to seven-membered ring of the formula:

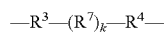

where k is an integer from 0 to 2, and $R^7$, where the ring is saturated, is $CH_2$, O, S, NH, $NH_2^+$, $NCH_2CH_2NH_2$, $NCH_2CH_2NH_3^+$, $NCH_2CH_2N(R^8)(R^9)$, $NCH_2CH_2N^+(R^8)(R^9)(R^{10})$, N(alkyl), N(aryl), N(benzyl), or $R^7$, where the ring is unsaturated is, N, $N^+H$, $N^+(alkyl)$, $N^+(aryl)$, $N^+(benzyl)$, $N-CH_2-N$, $N^+H-CH_2-N$, $N^+(alkyl)-CH_2-N$, $N^+(aryl)-CH_2-N$, or $N^+(benzyl)-CH_2-N$;

where $R^8$, $R^9$, and $R^{10}$ are, independently, benzyl, polyether, lower alkyl alcohol from 1 to 4 carbon atoms, lower alkoxy from 1 to 4 carbon atoms, or alkyl from 1 to about 22 carbon atoms, preferably 1 to about 10 carbon atoms;

$R^5$ is $CH_2C_6H_5$, $CH_2CH_2OH$, $CH_2CH(OH)CH_3$, a polyether such as polyethyleneglycol: $-(CH_2CH_2O)_aH$, polypropyleneglycol: $-(CH_2CH(CH_3)O)_aH$, or alkylated polyoxyethylene: $-(CH_2CH_2O)_aB$ where B is alkyl from 1 to 22 carbon atoms, unsubstituted or substituted, and where each a is, independently, an integer from 1 to 12, more preferably from about 1 to about 5, or $R^5$ is alkyl or perfluoroalkyl from 1 to about 22 carbon atoms, preferably from about 12 to about 20 carbon atoms and even more preferably from 14 to about 18 carbon atoms; and Y is halogen (such as Cl, Br, I), acetate, sulfate, tosylate or carboxylate, such as acetate, polycarboxylate salts, alcoholates, functionalized carboxylate, such as trifluoroacetate and perfluoroalkylcarboxylates, or other alkyl and arylsulfonate salts, including trifluoromethylsulfonate and anionic metal oxides, perfluoroalkylsulfonate salts, phosphate and phosphonate salts, borate and boronate salts, benzoates or any other suitable anionic moiety, and the ring provided for formula V represents $R^3$ or $R^4$, independently, with the ring nitrogen of formula I or II replaced by CH or $CH_2$. This ring is attached to the nitrogen in structure I or II, by removing any one hydrogen from the structure and placing a bond from the nitrogen of I or II to the atom missing the hydrogen.

Preferred organosilanes include, but are not limited to:
3-(trimethoxysilyl)propyldimethyloctadecyl ammonium chloride,
3-(trimethoxysilyl)propylmethyldi(decyl)ammonium chloride,
3-chloropropyltrimethylsilane,
octadecyltrimethoxysilane,
perfluorooctyltriethoxysilane,
$(CH_3O)_3Si(CH_2)_3N^+(CH_3)_2C_{18}H_{37}Cl^-$,
$(CH_3O)_3Si(CH_2)_3N^+(CH_3)_2C_{18}H_{37}Br^-$,
$(CH_3O)_3Si(CH_2)_3N^+(C_{10}H_{21})CH_3Cl^-$,
$(CH_3O)_3Si(CH_2)_3N^+(CH_{10}H_{21})CH_3Bf^-$,
$(CH_3O)_3Si(CH_2)_3N^+(CH_3)_3Cl^-$,
$(CH_3O)_3Si(CH_2)_3N^+(CH_3)_2C_8H_{17}Cl^-$,
$(CH_3O)_3Si(CH_2)_3N^+(CH_3)_2C_{10}H_{21}Cl^-$,
$(CH_3O)_3Si(CH_2)_3N^+(CH_3)_2C_{12}H_{25}Cl^-$,
$(CH_3O)_3Si(CH_2)_3N^+(CH_3)_2C_{14}H_{29}Cl^-$,
$(CH_3O)_3Si(CH_2)_3N^+(CH_3)_2C_{16}H_{33}Cl^-$,
$(CH_3O)_3Si(CH_2)_3N^+(CH_3)_2C_{20}H_{41}Cl^-$,
$(CH_3O)_3Si(CH_{12})_3N^+(C_4H_9)_3Cl^-$,
$(CH_3O)_3Si(CH_2)_3N^+(C_2H_5)_3Cl^-$,
$(CH_3CH_2O)_3Si(CH_2)_3N(CH_3)_2C_{18}H_{27}Cl^-$,
$(CH_3O)_3Si(CH_2)_3NHC(O)(CF_2)_6CF_3$,
$(CH_3O)_3Si(CH_2)_3NHC(O)(CF_2)_8CF_3$,
$(CH_3O)_3Si(CH_2)_3NHC(O)(CF_2)_{10}CF_3$,
$(CH_3O)_3Si(CH_2)_3NHC(O)(CF_2)_{12}CF_3$,
$(CH_3O)_3Si(CH_2)_3NHC(O)(CF_2)_{14}CF_3$,
$(CH_3O)_3Si(CH_2)_3NHC(O)(CF_2)_{16}CF_3$,
$(CH_3O)_3Si(CH_2)_3NHSO_2(CF_2)_7CF_3$,
$(CH_3O)_3Si(CH_2)_3N^+(CH_3)_2(CH_2)_3NHC(O)(CH_2)_6CH_3$,
$(CH_3O)_3Si(CH_2)_3N^+(CH_3)_2(CH_2)_3NHC(O)(CH_2)_8CH_3$,
$(CH_3O)_3Si(CH_2)_3N^+(CH_3)_2(CH_2)_3NHC(O)(CH_2)10CH_3$,
$(CH_3O)_3Si(CH_2)_3N^+(CH_3)_2(CH_2)_3NHC(O)(CH_2)12CH_3$,
$(CH_3O)_3Si(CH_2)_3N^+(CH_3)_2(CH_2)_3NHC(O)(CH_2)_{14}CH_3$,
$(CH_3O)_3Si(CH_2)_3N^+(CH_3)_2(CH_2)_3NHC(O)(CH_2)_{16}CH_3$,
$(CH_3O)_3Si(CH_2)_3N^+(CH_3)_2(CH_2)_3NHC(O)(CF_2)_6CF_3$,
$(CH_3O)_3Si(CH_2)_3N^+(CH_3)_2(CH_2)_3NHC(O)(CF_2)_8CF_3$,
$(CH_3O)_3Si(CH_2)_3N^+(CH_3)_2(CH_2)_3NHC(O)(CF_2)_{10}CF_3$,
$(CH_3O)_3Si(CH_2)_3N^+(CH_3)_2(CH_2)_3NHC(O)(CF_2)_{12}CF_3$, $(CH_3O)_3Si(CH_2)_3N^+(CH_3)_2(CH_2)_3NHC(O)(CF_2)_{14}CF_3$,
$(CH_3O)_3Si(CH_2)_3N^+(CH_3)_2(CH_2)_3NHC(O)(CF_2)_{16}CF_3$,
$(CH_3O)_3Si(CH_2)_3N^+(CH_3)_2(CH_2)_3NHSO_2(CF_2)_7CF_3$,
$(CH_3O)_3Si(CH_2)_3N^+(CH_3)_2(CH_2)_3NHSO_2(CF_2)_9CF_3$,
$(CH_3O)_3Si(CH_2)_3N^+(CH_3)_2(CH_2)_3NHSO_2(CF_2)_{11}CF_3$,
$(CH_3O)_3Si(CH_2)_3N^+(CH_3)_2(CH_2)_3NHSO_2(CF_2)_{13}CF_3$,
$(CH_3O)_3Si(CH_2)_3N^+(CH_3)_2(CH_{12})_3NHSO_2(CF_2)_{15}CF_3$,
$(CH_3O)_3Si(CH_2)_3N^+(CH_3)_2(CH_2)_3NHSO_2(CF_2)_{16}CF_3$,
aminoethylaminopropyltrimethoxysilane: $NH_2(CH_2)_2NH(C_1H_2)_3Si(OCH_3)_3$,
3-aminopropyltrimethoxysilane: $NH_2(CH_2)_3Si(OCH_3)_3$,
3-aminopropyltriethoxysilane: $NH_2(CH_2)_3Si(OCH_2CH_3)_3$,
3-chloropropyltrimethoxysilane: $Cl(CH_2)_3Si(OCH_3)_3$,
3-chloropropyltriethoxysilane: $Cl(CH_2)_3Si(OCH_2CH_3)_3$,
3-chloropropyltrichlorosilane: $Cl(CH_2)_3SiCl_3$,
3-glycidoxypropyltrimethoxysilane: $C_3H_5O_2(CH_2)_3Si(OCH_3)_3$,
3-glycidoxypropyltriethoxysilane: $C_3H_5O_2(CH_2)_3Si(OCH_2CH_3)_3$,
3-methacryloxypropyltrimethoxysilane: $C_4H_5O_2(CH_2)_3Si(OCH_3)_3$,
3-methacryloxypropyltriethoxysilane: $C_4H_5O_2(CH_2)_3Si(OC_2CH_3)_3$,
methyldichlorosilane: $CH_3SiHCl_2$,
silane-modified melamine: Dow Corning Q1-6106,
sodium (trihydroxysilyl)propylmethylphosphonate: $NaO(CH_3O)P(O)(CH_2)_3Si(OH)_3$,
trichlorosilane, $SiHCl_3$,
n-2-vinylbenzylamino-ethyl-3-aminopropyltrimethoxysilane HCL: Dow Corning Z-6032,
vinyltriacetoxysilane: $H_2C=CHSi(OCOCH_3)_3$,
vinyltrimethoxysilane: $H_2C=CHSi(OCH_3)_3$,
vinyltriethoxysilane: $H_2C=CHSi(OCH_2CH_3)_3$,
vinyltrichlorosilane: $H_2C=CHSiCl_3$,
dimethyldichlorosilane: $(CH_3)_2SiCl_2$,
dimethyldimethoxysilane: $(CH_3)_2Si(OCH_3)_2$,
diphenyldichlorosilane: $(C_6H_5)_2SiCl_2$,
ethyltrichlorosilane: $(C_2H_5)SiCl_3$,
ethyltrimethoxysilane: $(C_2H_5)Si(OCH_3)_3$,
ethyltriethoxysilane: $(C_2H_5)Si(OCH_2CH_3)_3$,
isobutyltrimethoxysilane,
n-octyltriethoxysilane,
methylphenyldichlorosilane: $CH_3(C_6H_5)SiCl_2$,
methyltrichlorosilane: $CH_3SiCl_3$,
methyltrimethoxysilane: $CH_3Si(OCH_3)_3$,
phenyltrichlorosilane: $C_6H_5SiCl_3$,
phenyltrimethoxysilane: $C_6H_5Si(OCH_3)_3$,
n-propyltriclorosilane: $C_3H_7SiCl_3$,
n-propyltrimethoxysilane: $C_3H_7Si(OCH_3)_3$,
silicon tetrachloride: $SiCl_4$,
$ClCH_2C_6H_4CH_2CH_2SiCl_{3n}$,
$ClCH_2C_6H_4CH_2CH_2Si(OCH_3)_3$,
$ClCH_2C_6H_4CH_2CH_2Si(OCH_2CH_3)_3$,
decyltrichlorosilane,
dichloromethyl(4-methylphenethyl)silane,
diethoxymethylphenylsilane,
[3-(diethylamino)propyl]trimethoxysilane,
3-(dimethoxymethylsilyl)-1-propanethiol,
dimethoxymethylvinylsilane,
3-[tris(trimethylsilyloxy)silyl]propyl methacrylate, trichloro[4-(chloromethyl)phenyl]silane,
methylbis(trimethylsilyloxy)vinylsilane,
methyltripropoxysilane, and
trichlorocyclopentylsilane.

In one particular embodiment of this invention, namely the use of the organosilane as a UV protectant, for example, in a suntan lotion, para-amino benzoic acid, cinnamic acid, benzoic acid and benzophenone are active ingredients. These compounds and their alkyl derivatives attached to a silane are part of this invention. Attachment of the aforementioned molecules is by removal of one atom or group from these compounds and utilizing this free valence for bond formation to a silane from which an atom or group has been removed also. Additional examples are:

$(CH_3O)_3Si(CH_2)_3NHC_6H_4COOH$,
$(CH_3O)_3Si(CH_2)_3NHC_6H_4COOCH_3$,
$(CH_3O)_3Si(CH_2)_3NHC_6H_4COOC_2H_5$,
$(CH_3O)_3Si(CH_2)_3NHC_6H_4COOC_3H_7$,
$(CH_3O)_3Si(CH_2)_3NHC_6H_4COOC_4H_9$,
$(CH_3O)_3Si(CH_2)_3NHC_6H_4COOCH_2C_6H_5$,
$(CH_3O)_3Si(CH_2)_3NHC_6H_4COOCH_2C_6H_4NH_2$,
$(CH_3O)_3Si(CH_2)_3NHC_6H_4COOCH_2C_6H_4N(CH_3)_2$,
$(CH_3O)_3Si(CH_2)_3NHC_6H_4COOCH_2C_6H_4N(CH_2CH_3)_2$,
$(CH_3O)_3Si(CH_2)_3NHC_6H_4COOCH_2C_6H_4N^+(CH_3)_3Y^-$,
$(CH_3O)_3Si(CH_2)_3NHC_6H_4COOCH_2C_6H_4N^+(CH_2CH_3)_3Y^-$,
$(CH_3O)_3Si(CH_2)_3NCH_3C_6H_4COOH$,
$(CH_3O)_3Si(CH_2)_3NCH_3C_6H_4COOCH_3$,
$(CH_3O)_3Si(CH_2)_3NCH_3C_6H_4COOC_2H_5$,
$(CH_3O)_3Si(CH_2)_3NCH_3C_6H_4COOC_3H_7$,
$(CH_3O)_3Si(CH_2)_3NCH_3C_6H_4COOC_4H_9$,
$(CH_3O)_3Si(CH_2)_3NCH_3C_6H_4COOCH_2C_6H_5$,
$(CH_3O)_3Si(CH_2)_3NCH_3C_6H_4COOCH_2C_6H_4NH_2$,
$(CH_3O)_3Si(CH_2)_3NCH_3C_6H_4COOCH_2C_6H_4N(CH_3)_2$,
$(CH_3O)_3Si(CH_2)_3NCH_3C_6H_4COOCH_2C_6H_4N(CH_2CH_3)_2$,
$(CH_3O)_3Si(CH_2)_3NCH_3C_6H_4COOCH_2C_6H_4N^+(CH_3)_3Y^-$,
$(CH_3O)_3Si(CH_2)_3NCH_3C_6H_4COOCH_2C_6H_4N^+(CH_2CH_3)_3Y^-$,
$(CH_3O)_3Si(CH_2)_3N^+(CH_3)_2C_6H_4COOH\ Y^-$,
$(CH_3O)_3Si(CH_2)_3N^+(CH_3)_2C_6H_4COOCH_3\ Y^-$,
$(CH_3O)_3Si(CH_2)_3N^+(CH_3)_2C_6H_4COOC_2H_5\ Y^-$,
$(CH_3O)_3SI(CH_2)_3N^+(CH_3)_2C_6H_4COOC_3H_7\ Y^-$,
$(CH_3O)_3SI(CH_2)_3N^+(CH_3)_2C_6H_4COOC_4H_9\ Y^-$,
$(CH_3O)_3SI(CH_2)_3N^+(CH_3)_2C_6H_4COOCH_2C_6H_5\ Y^-$,
$(CH_3O)_3Si(CH_2)_3N^+(CH_3)_2C_6H_4COOCH_2C_6H_4NH_2\ Y^-$,
$(CH_3O)_3Si(CH_2)_3N^+(CH_3)_2C_6H_4COOCH_2C_6H_4N(CH_3)_2Y^-$,
$(CH_3O)_3Si(CH_2)_3N^+(CH_3)_2C_6H_4COOCH_2C_6H_4N(CH_2CH_3)_2Y^-$,
$(CH_3O)_3Si(CH_2)_3N^+(CH_3)_2C_6H_4COOCH_2C_6H_4N^+(CH_3)_3Y^-Y^-$,
$(CH_3O)_3Si(CH_2)_3N^+(CH_3)_2C_6H_4COOCH_2C_6H_4N^+(CH_2CH_3)_3Y^-Y^-$,
$(CH_3O)_3Si(CH_2)_3NC_2H_5C_6H_4COOH$,
$(CH_3O)_3Si(CH_2)_3NC_2H_5C_6H_4COOCH_3$,
$(CH_3O)_3Si(CH_2)_3NC_2H_5C_6H_4COOC_4H_9$,
$(CH_3O)_3Si(CH_2)_3NC_2H_5C_6H_4COOC_3H_7$,
$(CH_3O)_3Si(CH_2)_3NC_2H_5C_6H_4COOC_4H_9$,
$(CH_3O)_3Si(CH_2)_3NC_2H_5C_6H_4COOCH_2C_6H_5$,
$(CH_3O)_3Si(CH_2)_3NC_2H_5C_6H_4COOCH_2C_6H_4NH_2$,
$(CH_3O)_3Si(CH_2)_3NC_2H_5C_6H_4COOCH_2C_6H_4N(CH_3)_2$,
$(CH_3O)_3Si(CH_2)_3NC_2H_5C_6H_4COOCH_2C_6H_4N(CH_2CH_3)_2$,
$(CH_3O)_3Si(CH_2)_3NC_2H_5C_6H_4COOCH_2C_6H_4N^+(CH_3)_3Y^-$,
$(CH_3O)_3Si(CH_2)_3NC_2H_5C_6H_4COOCH_2C_6H_4N^+(CH_2CH_3)_3Y^-$,
$(CH_3O)_3Si(CH_2)_3N^+(C_2H_5)_2C_6H_4COOH\ Y^-$,
$(CH_3O)_3Si(CH_2)_3N^+(C_2H_5)_2C_6H_4COOCH_3Y^-$,
$(CH_3O)_3Si(CH_2)_3N^+(C_2H_5)_2C_6H_4COOC_2H_5Y^-$,
$(CH_3O)_3Si(CH_2)_3N^+(C_2H_5)_2C_6H_4COOC_3H_7Y^-$,
$(CH_3O)_3Si(CH_2)_3N^+(C_2H_5)_2C_6H_4COOC_4H_9Y^-$,
$(CH_3O)_3Si(CH_2)_3N^+(C_2H_5)_2C_6H_4COOCH_2C_6H_5Y^-$,
$(CH_3O)_3Si(CH_2)_3N^+(C_2H_5)_2C_6H_4COOCH_2C_6H_5N_2Y^-$,
$(CH_3O)_3Si(CH_2)_3N^+(C_2H_5)_2C_6H_4COOCH_2C_6H_4N(CH_3)_2Y^-$, $(CH_3O)_3Si(CH_2)_3N^+(C_2H_5)_2C_6H_4COOCH_2C_6H_4N(CH_2CH_3)_2Y^-$,
$(CH_3O)_3Si(CH_2)_3N^+(C_2H_5)_2C_6H_4COOCH_2C_6H_4N^+(CH_3)_3Y^-Y^-$,
$(CH_3O)_3Si(CH_2)_3N^+(C_2H_5)_2C_6H_4COOCH_2C_6H_4N^+(CH_2CH_3)_3Y^-Y^-$,
$(CH_3CH_2O)_3Si(CH_2)_3NHC_6H_4COOH$,
$(CH_3CH_2O)_3Si(CH_2)_3NHC_6H_4COOCH_3$,
$(CH_3CH_2O)_3Si(CH_2)_3NHC_6H_4COOC_2H_5$,
$(CH_3CH_2O)_3Si(CH^2)_3NHC_6H_4COOC_3H_7$,
$(CH_3CH_2O)_3Si(CH_2)_3NHC_6H_4COOC_4H_9$,
$(CH_3CH_2O)_3Si(CH_2)_3NHC_6H_4COOCH_2C_6H_5$,
$(CH_3CH_2O)_3Si(CH_2)_3NHC_6H_4COOCH_2C_6H_4NH_2$,
$(CH_3CH_2O)_3Si(CH_2)_3NHC_6H_4COOCH_2C_6H_4N(CH_3)_2$
$(CH_3CH_2O)_3Si(CH_2)_3NHC_3H_4COOCH_2C_6H_4N(CH_2CH_3)_2$,
$(CH_3CH_2O)_3Si(CH_2)_3NHC_6H_4COOCH_2C_6H_4N^+(CH_3)_3Y^-$,
$(CH_3CH_2O)_3Si(CH_2)_3NHC_6H_4COOCH_2C_6H_4N^+(CH_2CH_3)_3Y^-$,
$(CH_3CH_2O)_3Si(CH_2)_3NCH_3C_6H_4COOH$,
$(CH_3CH_2O)_3Si(CH_2)_3NCH_3C_6H_4COOCH_3$,
$(CH_3CH_2O)_3Si(CH_2)_3NCH_3C_6H_4COOC_2H_5$,
$(CH_3CH_2O)_3Si(CH_2)_3NCH_3C_6H_4COOC_3H_7$,
$(CH_3CH_2O)_3Si(CH_2)_3NCH_3C_6H_4COOC_4H_9$,
$(CH_3CH_2O)_3Si(CH_2)_3NCH_3C_6H_4COOCH_2C_6H_5$,
$(CH_3CH_2O)_3Si(CH_2)_3NCH_3C_6H_4COOCH_2C_6H_4NH_2$,
$(CH_3CH_2O)_3Si(CH_2)_3NCH_3C_6H_4COOCH_2C_6H_4N(CH_3)_2$,
$(CH_3CH_2O)_3Si(CH_2)_3NCH_3C_6H_4COOCH_2C_6H_4N(CH_2CH_3)_2$,
$(CH_3CH_2O)_3Si(CH_2)_3NCH_3C_6H_4COOCH_2C_6H_4N^+(CH_3)_3Y^-$,
$(CH_3CH_2O)_3Si(CH_2)_3NCH_3C_6H_4COOCH_2C_6H_4N^+(CH_2CH_3)_3Y^-$,
$(CH_3CH_2O)_3Si(CH_2)_3N^+(CH_3)_2C_6H_4COOH\ Y^-$,
$(CH_3CH_2O)_3Si(CH_2)_3N^+(CH_3)_2C_6H_4COOCH_3Y^-$,
$(CH_3CH_2O)_3Si(CH_2)_3N^+(CH_3)_2C_6H_4COOC_2H_5Y^-$,
$(CH_3CH_2O)_3Si(CH_2)_3N^+(CH_3)_2C_6H_4COOC_3H_7Y^-$,
$(CH_3CH_2O)_3Si(CH_2)_3N^+(CH_3)_2C_6H_4COOC_4H_9Y^-$,
$(CH_3CH_2O)_3Si(CH_2)_3N^+(CH_3)_2C_6H_4COOCH_2C_6H_5Y^-$,
$(CH_3CH_2O)_3Si(CH_2)_3N^+(CH_3)_2C_6H_4COOCH_2C_6H_4NH_2Y^-$,
$(CH_3CH_2O)_3Si(CH_2)_3N^+(CH_3)_2C_6H_4COOCH_2C_6H_4N(CH_3)_2Y^-$,
$(CH_3CH_2O)_3Si(CH_2)_3N^+(CH_3)_2C_6H_4COOCH_2C_6H_4N(CH_2CH_3)_2Y^-$,
$(CH_3CH_2O)_3Si(CH_2)_3N^+(CH_3)_2C_6H_4COOCH_2C_6H_4N^+(CH_3)_3Y^-Y^-$,
$(CH_3CH_2O)_3Si(CH_2)_3N^+(CH_3)_2C_6H_4COOCH_2C_6H_4N^+(CH_2CH_3)_3Y^-Y^-$,
$(CH_3CH_2O)_3Si(CH_2)_3NC_2H_5C_6H_4COOH$,
$(CH_3CH_2O)_3Si(CH_2)_3NC_2H_5C_6H_4COOCH_3$,
$(CH_3CH_2O)_3Si(CH_2)_3NC_2H_5C_6H_4COOC_2H_5$,
$(CH_3CH_2O)_3Si(CH_2)_3NC_2H_5C_6H_4COOC_3H_7$,
$(CH_3CH_2O)_3Si(CH_2)_3NC_2H_5C_6H_4COOC_4H_9$,
$(CH_3CH_2O)_3Si(CH_2)_3NC_2H_5C_6H_4COOCH_2C_6H_5$,
$(CH_3CH_2O)_3Si(CH_2)_3NC_2H_5C_6H_4COOCH_2C_6H_4NH_2$,
$(CH_3CH_2O)_3Si(CH_2)_3NC_2H_5C_6H_4COOCH_2C_6H_4N(CH_3)_2$,
$(CH_3CH_2O)_3Si(CH_2)_3NC_2H_5C_6H_4COOCH_2C_6H_4N(CH_2CH_3)_2$,
$(CH_3CH_2O)_3Si(CH_2)_3NC_2H_5C_6H_4COOCH_2C_6H_4N^+(CH_3)_3Y^-$,
$(CH_3CH_2O)_3Si(CH_2)_3NC_2H_5C_6H_4COOCH_2C_6H_4N^+(CH_2CH_3)_3Y^-$,
$(CH_3CH_2O)_3Si(CH_2)_3N^+(C_2H_5)_2C_6H_4COOH\ Y^-$,
$(CH_3CH_2O)_3Si(CH_2)_3N^+(C_2H_5)_2C_6H_4COOCH_3Y^-$,
$(CH_3CH_2O)_3Si(CH_2)_3N^+(C_2H_5)_2C_6H_4COOC_2H_5Y^-$,
$(CH_3CH_2O)_3Si(CH_2)_3N^+(C_2H_5)_2C_6H_4COOC_3H_7Y^-$,
$(CH_3CH_2O)_3Si(CH_2)_3N^+(C_2H_5)_2C_6H_4COOC_4H_9Y^-$,
$(CH_3CH_2O)_3Si(CH_2)_3N^+(C_2H_5)_2C_6H_4COOCH_2C_6H_5Y^-$,
$(CH_3CH_2O)_3Si(CH_2)_3N^+(C_2H_5)_2C_6H_4COOCH_2C_6H_4NH_2Y^-$,
$(CH_3CH_2O)_3Si(CH_2)_3N^+(C_2H_5)_2C_6H_4COOCH_2C_6H_4N(CH_3)_2Y^-$,
$(CH_3CH_2O)_3Si(CH_2)_3N^+(C_2H_5)_2C_6H_4COOCH_2C_6H_4N(CH_2CH_3)_2Y^-$,
$(CH_3CH_2O)_3Si(CH_2)_3N^+(C_2H_5)_2C_6H_4COOCH_2C_6H_4N^+(CH_3)_3Y^-Y^-$, and
$(CH_3CH_2O)_3Si(CH_2)_3N^+(C_2H_5)_2C_6H_4COOCH_2C_6H_4N^+(CH_2CH_3)_3Y^-Y^-$.

Uses

The compounds, products, and compositions of the present invention are useful for a multitude of purposes. Such purposes include any known use for the preferred starting material organosilanes of the above-described general formula. In preferred embodiments, the presently described water-stabilized, organosilane compounds, products, and compositions are suitable to applications such as: 1) treatment of surfaces, including fillers and pigments, 2) additives to coatings such as dyes, 3) additives to organic monomers (such as acrylics) prior to formation of the respective polymer, 4) addition to the polymer prior to processing into final products or 5) incorporation into polymer or substrate backbone, such as polyester or concrete.

Therefore, in addition to the utility of prior organosilane quaternary ammonium compounds, for example, 3-(trimethoxysilyl)propyl-dimethyloctadecyl ammonium chloride useful as surface bonding antimicrobial agents, numerous other uses of organofunctional silanes are contemplated, such as the use of the compounds, products and compositions of the invention in coating applications including the treatment of surfaces or particles (pigments or fillers), in primers, in paints, inks, dyes and adhesives, and as reactive intermediates for silicone resin synthesis.

The present invention can be used to prepare, inter alia, agricultural products, cleaning compositions, antimicrobial sponges, antimicrobial bleaching agents, antimicrobial fillers for paints, plastics, or concrete, and to treat concrete structures such as livestock shelters, where microbial infestation is a problem.

In various embodiment, surfaces and substrates treatable with the compounds, products and compositions of the invention solution include, but are not limited to, textiles, carpet, carpet backing, upholstery, clothing, sponges, plastics, metals, surgical dressings, masonry, silica, sand, alumina, aluminum chlorohydrate, titanium dioxide, calcium carbonate, wood, glass beads, containers, tiles, floors, curtains, marine products, tents, backpacks, roofing, siding, fencing, trim, insulation, wall-board, trash receptacles, outdoor gear, water purification systems, and soil. Furthermore, articles treatable with the compounds, products and compositions of the invention include, but are not limited to, air filters and materials used for the manufacture thereof, aquarium filters, buffer pads, fiberfill for upholstery, fiberglass ductboard, underwear and outerwear apparel, polyurethane and polyethylene foam, sand bags, tarpaulins, sails, ropes, shoes, socks, towels, disposal wipes, hosiery and intimate apparel, cosmetics, lotions, creams, ointments, disinfectant sanitizers, wood preservatives, plastics, adhesives, paints, pulp, paper, cooling water, and laundry additives and non-food or food contacting surfaces in general.

For the above described substrates, mixtures and applications, treatment generally involves contacting or mixing the article to be treated with a water-stabilized organosilane solution of the present invention, comprising the organosilane-stabilizer derived compound in an aqueous solution, for a period of time sufficient for permanent bonding of the active organosilane ingredient (or portion thereof) to the article. In alternative embodiments, organosilane-acidified stabilizing solution mixtures in accordance with the present invention can be used directly without dilution with water, or, alternatively, with dilution with solvents other than water. Generally, treatment begins almost immediately upon contact. Preferably, treatment requires from about 15 seconds to about 48 hours. More preferably, treatment requires from about 1 minute to about 24 hours. Even more preferably, treatment requires from about five minutes to 1 hour and most preferably, treatment requires about 30 minutes. Further general guidelines for application are as follows: For dipping a large object, it is preferred that about 1 to about 3 minutes of submersion is allowed in the solution, and then, the object is permitted to dry or is dried. However, some objects will benefit from very short dipping, mixing or contacting times. For example, fabric may pass through an aqueous bath of the composition at a rate of up to 40 yards per minute or more. After dipping, excess solution may be gently wiped or rinsed off. Alternatively, the solution may be sprayed on to the substrate. Moreover, the composition of the invention maybe placed in a high intensity solid mixer and formed into a powder, which is then dried. The dried powder may then be used in a sprayer, if desired. In addition, the solutions may be wiped onto the substrate and applied using sponges or cloths, etc. Moreover, the solutions of the present invention can be added to pigments and fillers and stirred therewith for several (2-3) minutes. In addition, the solutions can be added to an emulsion or other existing formulation prior to use. Also, the solutions can be used in addition to, with, or as a spray coolant for extruded fibers. However, one of ordinary skill in the art would recognize that numerous other uses and modes of application are readily apparent from the stabilized organosilane compounds, products and compositions of the present invention and would, without undue experimentation, be able to determine effective application methods and treating times for any particular substrate, article, or other application. In addition, the compositions can be used in padding processes as are known in textile mills.

Moreover, after treating a surface or fabric with the compound, product, or compositions of the present invention, the surface or fabric may, optionally, be heated to further complete bonding of the compound, product, or composition to the surface or substrate.

The water-stable organosilane compounds, products, and compositions of the present invention are, therefore, advantageous in treating a variety of substrates without the use of toxic organic solvents and provide for the safe, long-term storage of activated organosilanol compound that can be used without further preparation. Moreover, the stabilization scheme described herein does not interfere with the binding of the organosilane (or at least the core, operative portion thereof) to the substrate. In addition, the present invention provides a generally applicable scheme for solvating some water insoluble organosilanes.

Also apparent will be those applications where organosilanes $R_nSiX_{4-n}$ are prepared, dissolved, stored, applied, and in any way used in water. Also apparent will be those applications of organosilanes $R_nSiX_{4-n}$, in other solvents or mixed in other media (solids, polymer mixes, fillers, pigments, powders, dyes or emulsions) where exposure to water occurs but could be detrimental due to undesired or untimely self-condensation of the silanol.

Moreover, the stabilizing compounds and methods could be used in addition to or in conjunction with various art-known stabilization methods for organosilanes, such as the use of ionic or non-ionic surfactants and detergents.

Moreover, the present compounds, products, and compositions can be used in the incorporation of an organosilane antimicrobial agent in most textile goods (woven and non-woven) and yarns (synthetic and natural). The process provides articles that are durable, and the process itself is effective and does not require additional manufacturing steps or increased manufacturing cost.

Incorporating the compounds, products, and compositions of the present invention during the dye process yields a textile material with a built-in antimicrobial agent with the organosilane characteristics, binding and antimicrobial protection. The incorporation process 1) does not add any additional step in the manufacturing process and does not require any equipment modification; and 2) is believed not to lose its antimicrobial characteristics and its effectiveness during further production of the textile goods. By incorporating the water-stable compounds, products and compositions of the present invention during the dye process, not only would the organosilane antimicrobial agent remain unaffected by the dying agent, but the end-product textile goods would also exhibit excellent dyeing properties.

The water-stabilized organosilane compounds, products, and compositions of the present invention are useful for a number of applications where the previous instability, insolubility prevented or, at least, hindered or restricted use of some organosilane agents. For example:

Treating food crops (for example, perishables such as vegetables, fruits, or grains) after removal (pickled/harvested) with the compounds, products and compositions of the present invention imparts antimicrobial protection to the outer surface of the food crop. It is believed that such protection occurs without diffusing, migrating or leaching the antimicrobial agent from the bonded antimicrobial coating of the food item and provides prolonged, safe and non-toxic antimicrobial protection. The method involves treating fruits and vegetables in the rinse cycle, during or after the normal cleaning/water spraying, or during or after blanching. Thorough cleaning of fruits and vegetables at the processing plant is preferred for initially removing microorganisms. As one of ordinary skill in the art would recognize, machines are used initially to remove soil, chemicals used in growing, spoilage bacteria, and other foreign materials. These machines also use high velocity water sprays to clean the products. After the cleaning, raw foods or other crop materials are prepared for further processing such as blanching where the food is immersed in water at 190° F. to 210° F. or exposed to steam.

Microorganisms are controlled by the production plant up until the fruit or vegetable is removed. But once it is removed, organisms such as yeast, mold, and bacteria begin to multiply, causing the food to loose flavor and change in color and texture. To keep the food from spoiling, a number of methods have been employed, such as refrigerators, to slow down the microorganisms and delay deterioration. Unfortunately, such known methods will preserve raw foods for a few weeks at most. The compounds, products, and compositions of the present invention can preserve these items for extended periods. For instance, the compositions, products, or compounds may be added to an existing water line feeding the sprayers for the foods, where such sprayers are used. Otherwise, a simple dipping process may be used, where the dipping requires only a few seconds to impart antimicrobial protection. Low concentrations of about 0.1 to about 1% aqueous solution (about 0.1 to about 1% by volume) of the compositions provide satisfactory results. In addition, it is believed that the presently described method can also control pathogens on poultry carcasses and in other susceptible meat and fish.

Treating baby milk/juice bottles, nipples, pacifiers and toys with the compounds, products and compositions of the present invention in the factory or leaching the agent from the bonded surface, can provide prolonged and safe/non-toxic antimicrobial protection. Treating such articles also eliminates odors caused by microbial contamination. A dipping method as described above may be used to treat these articles.

To date, parents have used soaps, detergents, and surface cleaners to alleviate the problems of contamination of these articles. However, these and other similar treatments have, for the most part, been inadequate and required repeated treatment. In addition, these treatments have been found to be limited in their ability to offer broad spectrum control of microorganisms. Therefore, the present compounds, products, and compositions can be used to treat these articles to prevent microbial growth and contamination by coating an effective amount of the products and compounds of the invention thereon. The articles employed can be coated by allowing for about 1 to about 2 minutes submersion, for example, by dipping, and thereafter, the treated surface is allowed to dry at room temperature. The article is then rinsed of any excess antimicrobial agent. Thorough cleaning and sterilization is a preferred step in removing the microorganisms on the surface of the article prior to "coating" the article. In addition, preferably concentrations of about 10% or more by volume of the compounds, products, and compositions of the invention are used for long lasting protection.

Treating surgical gloves with the compounds, products and compositions of the present invention before or during a surgical procedure can kill microorganisms on contact. It is believed that the treated gloves diffuse or leach the antimicrobial agent from the glove surface and provide prolonged antimicrobial activity with safe and non-toxic antimicrobial protection. Surgical gloves are treated, preferably, by submerging in the solution of the example, diluted to 1% W/V for at least 30 seconds. This method will permit doctors to use and, if necessary, re-use the same gloves (even without removing them) without undue fear of contamination.

Treating polymers and other materials such as concrete by incorporation into the bulk material protects from deterioration, odor build-up and potentially harmful contamination of the surface. Incorporation of a sun protection into polymers extends the life of the product.

Moreover, one of ordinary skill in the art would be able to implement numerous other end uses based upon the disclosure of the compounds, products and compositions of the present invention. Some uses require aqueous solutions, and some require non-aqueous environments. However, both applications are part of the invention. Furthermore, antimicrobial properties of the silane compounds according to the invention are only one of many possible properties. Mixtures of silanes according to the invention often provide additional benefits.

For instance, the following uses, applications and substrates, are contemplated:
1. Concrete, Concrete Water Conduits, Storm and Sewer Pipes treated with the compounds, products and compositions of the present invention. Agents to kill microorganism on contact and provide prolonged antimicrobial protection to prevent deterioration of the concrete and its coatings.
2. Tooth Brushes, Combs, Hair Brushes, Dentures and Retainers
3. Spa and Pool Filters meeting stringent requirements that no other antimicrobial agent can meet and protection for Air Filtration such as air conditioning filters, HVAC applications and cabin air
4. Marble Slabs (building facia, tombs, floors) treated with the compounds, products and compositions of the present invention
5. Rubbing Alcohol
6. Statues and Exposed Art Work
7. HDP (high density polyester) fabric plastic covers for dump sites, water reservoirs and generally for soil protection
8. Liquid Additive (as flower water preservative for potted plants and cut flowers)
9. Silicone and TEFLON coated Fiberglass with antimicrobial protection including acrylic backing wall covering
10. Dryvitt and Stucco finish
11. Waterproofing treated with the compounds, products and compositions of the present invention
12. A method of treating blended cotton before or after picking machines make the cotton into rolls or laps
13. Food Packaging and Containers
14. Bio-films and adhesives (tapes and silicone wafers)
15. Single Ply Roofing and Roof shingles
16. Fiberglass Reinforcement Product The preferred embodiments of the above-described water-stabilized antimicrobial compounds, products, compositions, and methods are set forth in the following example. Other features of the invention will become apparent from the following examples, which is for illustrative purposes only and are not intended as a limitation upon the present invention.

EXAMPLE 1

Non-Acidic Stabilizing Solutions

Five different antimicrobial organosilane-based compositions were prepared and exposed to different storage temperatures. Composition A is a 10% active composition containing 10 wt % 3-(trimethoxysilyl)propyldimethyloctadecyl ammonium chloride, 2 wt % N-alkyl,N,N dimethyl N benzylammonium chloride (CAS #68424-85-1), 2 wt % diethylene glycol butyl ether, and water. The composition was not acidic. A portion of composition A was stored in a refrigerator cooled to 2° C. for approximately 27½ hours after which the color of composition A was white, similar to milk. The white color indicated that the 3-(trimethoxysilyl)propyldimethyloctadecyl ammonium chloride self-condensed. A second portion of composition A was stored at 60° C. for approximately 28 hours after which the composition remained clear in color. The clear color indicated that the 3-(trimethoxysilyl)propyldimethyloctadecyl ammonium chloride did not self-condense.

Composition B is a 15% active composition containing 15 wt % 3-(trimethoxysilyl)propyldimethyloctadecyl ammonium chloride, 2 wt % N-alkyl,N,N dimethyl N benzylammonium chloride (CAS #68424-85-1), 2 wt % diethylene glycol butyl ether, and water. The composition was not acidic. A first portion of composition B was stored in a refrigerator cooled to 2° C. for approximately 27½ hours after which the color of composition B was while, similar to milk. A second portion of composition B was stored at 60° C. for approximately 28 hours after which the color remained clear. Again, a white color indicated that the 3-(trimethoxysilyl)propyldimethyloctadecyl ammonium chloride self-condensed, and a clear liquid indicated that the 3-(trimethoxysilyl)propyldimethyloctadecyl ammonium chloride did not self-condense.

Composition B was further modified in three different ways. Composition $B_g$ was prepared by adding one drop of glycerine to 5 mls of composition B and was stored at 60° C. After approximately 23½ hours, composition $B_g$ remained clear. Composition $B_g$ was then stored for approximately 24½ hours in a refrigerator cooled to 2° C. During the cooled storage, the composition became slightly viscous and milky white in color. The combination of the slightly viscous thickness and the milky white color indicated that the 3-(trimethoxysilyl)propyldimethyloctadecyl ammonium chloride self-condensed.

A second sample of composition $B_g$ was stored in a refrigerator cooled to 2° C. for approximately 17 hours. The composition was clear and did not appear to be viscous. The second sample was returned to cold storage in a 2° C. refrigerator and after approximately 17 hours became slightly viscous and milky white in color. Again, the combination of the slightly viscous thickness and the milky white color indicated that the 3-(trimethoxysilyl)propyldimethyloctadecyl ammonium chloride self-condensed.

Composition $B_v$ was prepared by adding one drop of VIDET Qx9 to 5 mls of composition B and initially was stored at a temperature of 60° C. VIDET Qx9 is a proprietary blend of cationic surfactants available from Vitech International, Inc. (Janesville, Wis.). After approximately 23½ hours in storage at 60° C., composition $B_v$ did not show signs of polymerization and was clear. The sample was then placed in a 2° C. refrigerator for approximately 24½, hours. The heated and then cooled sample began to show signs of polymerization. It was milky white in color and slightly viscous, which indicated that the 3-(trimethoxysilyl)propyldimethyloctadecyl ammonium chloride self-condensed.

A second sample of composition $B_v$ was stored for approximately 17 hours in a 2° C. refrigerator, and the sample remained clear. The sample was again stored for about 17 hours in a 2° C. refrigerator, remained clear, and did not polymerize.

Composition $B_m$ was prepared by adding 10 mg of monopentaerythritol (MPE) to 5 mls of composition B and stored at 60° C. for approximately 23½ hours. Composition $B_m$ remained clear and was then stored in a refrigerator cooled to 2° C. The heated and then cooled composition was slightly viscous and milky white in color indicating polymerization of 3-(trimethoxysilyl)propyldimethyloctadecyl ammonium chloride.

A second sample of composition $B_m$ was stored overnight in a refrigerator cooled to 2° C. After about 17 hours, the composition was clear. It was again stored in a refrigerator cooled to 2° C. for about 17 hours, and the color changed to a white similar to the color of milk. The white color indicates that the 3-(trimethoxysilyl)propyldimethyloctadecyl ammonium chloride polymerized.

EXAMPLE 2

Varying the Type of Surfactant in the Stabilizing Solution

Six different antimicrobial organosilane compositions were prepared with different combinations of surfactants in the stabilizing solution. Composition C, a 15% active composition, was prepared from 20.83 grams of 3-(trim ethoxysilyl)propyldimethyloctadecyl ammonium chloride mixed with a stabilizing solution consisting of 1.5 grams of VIDET Qx9 (Janesville, Wis.), 1.5 grams of N-alkyl,N,N dimethyl N benzylammonium chloride (CAS #68424-85-1), and 2.0 grams diethylene glycol butyl ether. VIDET Qx9 is a cationic surfactant blend obtained from Vitech International Inc. A first sample of composition C was stored in a refrigerator cooled to 2° C., and a second sample was stored at 60° C. The cold storage sample was milky white in color after about 24 hours. The heated storage sample was thin and clear after about 28 hours. Again, the milky white color of the frozen sample indicated that the 3-(trimethoxysilyl)propyldimethyloctadecyl ammonium chloride self-condensed, and the clearness of the heated sample indicated that the 3-(trimethoxysilyl)propyldimethyloctadecyl ammonium chloride did not self-condense.

Composition D, a 15% active composition, was prepared from 20.83 grams of (3-(trimethoxysilyl)propyldimethyloctadecyl ammonium chloride), 1.5 grams of AMPHOTERGE LF (Lonza Inc.; Allendale, N.J.), 1.5 grams of N-alkyl,N,N dimethyl N benzylammonium chloride (CAS #68424-85-1), and 2.0 grams of diethylene glycol butyl ether. AMPHOTERGE LF is a capryl substituted imidazoline amphoteric low-foaming surfactant. It has a specific gravity of 1.084, a density of 9 pounds per gallon, and is a clear yellow liquid. Two samples of composition D were stored for 24 hours at 2° C. and 60° C., respectively. Each sample of composition D was milky white in color regardless of the storage temperature indicating that the 3-(trimethoxysilyl)propyldimethyloctadecyl ammonium chloride was polymerizing.

Composition E, a 15% active composition, was prepared from 20.83 grams of 3-(trimethoxysilyl)propyldimethyloctadecyl ammonium chloride mixed with a stabilizing solution consisting of 4.0 grams of VIDET Qx9, 1.0 gram of AMPHOTERGE LU, 1.0 gram of N-alkyl,N,N dimethyl N benzylammonium chloride (CAS #68424-85-1), and 2.0 grams of diethylene glycol butyl ether. Two samples of composition E were stored in two different storage temperatures—2° C. and 60° C. Regardless of storage temperature, the composition became milky white after 24 hours. The color represents self-condensation of the 3-(trimethoxysilyl)propyldimethyloctadecyl ammonium chloride.

Composition F was prepared from 13.9 grams of 3-(trimethoxysilyl)propyldimethyloctadecyl ammonium chloride mixed with a stabilizing solution consisting of 1.5 VIDET Qx9, 1.5 grams of N-alkyl,N,N dimethyl N benzylammonium chloride (CAS #68424-85-1), and 2.0 grams of diethylene glycol butyl ether and is a 10% active composition. Composition F was stored at 60° C., and particulates were observed in the composition after about 28 hours. The presence of particulates indicated that the 3-(trimethoxysilylpropyldimethyloctadecyl ammonium chloride started polymerizing.

The 10% active composition G was prepared from 13.9 grams of the antimicrobial compound, 3-(trimethoxysilyl) propyldimethyloctadecyl ammonium chloride, mixed with a stabilizing solution consisting of 1-5 grams of AMPHOTERGE LF, 1.5 grams of N-alkyl,N,N dimethyl N benzylammonium chloride (CAS #68424-85-1), and 2.0 grams of diethylene glycol butyl ether. Composition G was stored at 60° C., and the composition was thin and clear, which indicates that the organosilane did not self-condense, after about 28 hours.

Composition H, a 10% active composition, was prepared from 13.9 grams of (3-(trimethoxysilyl)propyldimethyloctadecyl ammonium chloride) mixed with a stabilizing solution consisting of 1.5 grams of VIDET Qx9, 1.5 grams of AMPHOTERGE LF, 1.5 grams of N-alkyl,N,N dimethyl N benzylammonium chloride (CAS #68424-85-1), and 2.0 grams of diethylene glycol butyl ether. Composition H was stored at 60° C., and particulates were observed in the composition after about 28 hours. The presence of particulates indicated that the 3-(trimethoxysilyl)propyldimethyloctadecyl ammonium chloride started polymerizing.

EXAMPLE 3

A stabilizing solution was prepared from 2 grams of N-alkyl,N,N dimethyl N benzylammonium chloride (CAS #68424-85-1), 57.17 grams of $H_2O$, and 20 grams of diethylene glycol butyl ether The pH was adjusted to 2 with an acid. The stabilizing solution was well mixed with light heat with 20.83 grams of 3-(trimethoxysilyl)propyldimethyloctadecyl ammonium chloride. After 20 days, the composition I was clear and thin indicating that 3-(trimethoxysilyl)propyldimethyloctadecyl ammonium chloride did not polymerize and was stable in the presence of water.

A second stabilizing solution was prepared from 2 grams of N-alkyl,N,N dimethyl N benzylammonium chloride (CAS #68424-85-1), 57.17 grams of $H_2O$, 20 grams of VIDET Q-3. The pH was adjusted to 2 with the addition of an acid. The stabilizing solution was well mixed with light heat with 20.83 grams of (3-(trimethoxysilyl)propyldimethyloctadecyl ammonium chloride). After 20 days, the composition J was clear and slightly viscous.

Compositions I and J were further studied in freeze and thaw tests. 5 mls of both compositions I and J were placed in a freezer. Three hours later, the samples were placed in a 50° C. oven to thaw. The thawed compositions were clear and thin.

Compositions I and J were frozen again for about 16 and a half hours before placed in a 50° C. oven to thaw a second time. Each composition was clear and thin after exposure to the 50° C. oven.

Compositions I and J were frozen for a third time for only an hour and a half and then thawed in a 50° C. oven. Composition I remained clear and thin, but composition J was milky white and thick. Composition I remained stable after three cycles of a freeze and thaw test, while composition J started to show signs of polymerization after three cycles of the test.

EXAMPLE 4

Stability of Compositions with Different Activities

The effect of the percentage of the active ingredient, 3-(trimethoxysilyl)propyldimethyloctadecyl ammonium chloride was investigated. Six compositions were prepared by first making a stabilizing solution from N-alkyl,N,N dimethyl N benzylammionium chloride, diethylene glycol butyl ether, either VIDET Q3 or ethoxylated nonylphenol, and water in the amounts listed in Table 1. VIDET Q3 is a non-ionic blend of surfactants available from Vitech International (Janesville, Wis.) whose appearance is clear to slightly turbid and pale yellow and has a pH between 6 and 9. The pH of the stabilizing solution was adjusted to 2 with the addition of a sufficient amount of acid, and the solution was mixed with the active ingredient to form compositions K-P. Observations of the stability of each composition in terms of color and viscosity were made after several days in storage.

TABLE 1

Compositions K-P

| | Composition | | | | | |
|---|---|---|---|---|---|---|
| | K | L | M | N | O | P |
| Antimicrobial Organosilane Activity | 15% | 15% | 20% | 20% | 25% | 25% |
| N-alkyl,N,N dimethyl N benzylammonium chloride (grams) | 2 | 2 | 2 | 2 | 2 | 2 |
| diethylene glycol butyl ether (grams) | 5 | 5 | 5 | 5 | 5 | 5 |
| VIDET Q3 (grams) | 15 | — | 15 | — | 15 | — |
| Ethoxylated nonylphenol (grams) | — | 15 | — | 15 | — | 15 |
| $H_2O$ (grams) | 56.93 | 56.93 | 50.08 | 50.08 | 42.9 | 42.9 |
| pH | 2 | 2 | 2 | 2 | 2 | 2 |
| 3-(trimethoxysilyl)propyl-dimethyloctadecyl ammonium chloride (grams) | 21.07 | 21.07 | 28.08 | 28.08 | 35.1 | 35.1 |

After 15 days in storage, composition K was thin and cloudy, but no white was visible in the liquid, composition M was thin and clear, but traces of white were beginning to appear in the liquid. Composition O was viscous and white in color.

After 12 days in storage, compositions L, N, and P were all thick and milky white suggesting that the additional ethoxylated nonylphenol to the stabilizing solution did not contribute to preventing self-condensation of the 3-(trimethoxysilyl)propyldimethyloctadecyl ammonium chloride.

EXAMPLE 5

Freeze/Thaw Studies

The effect of the percentage of the active ingredient, 3-(trimethoxysilyl)propyldimethyloctadecyl ammonium chloride during freeze/thaw studies was investigated. Compositions Q-U were each prepared by first adding together N-alkyl,N,N dimethyl N benzylammonium chloride, diethylene glycol butyl ether, and deionized $H_2O$, adjusting the pH to 2.5 with the addition of several drops of $1\underline{M}$ HCl (9 drops for compositions Q-S, and 2 drops for compositions T and U), adding the active ingredient, and mixing together for 10 minutes. The amounts of each component other than the acid are given in Table 2 below.

5 ml samples of compositions Q-U underwent freeze/thaw testing. This entailed freezing and then thawing the samples at 55° C., refreezing the samples for 1½ hours, and again thawing at 55° C., and freezing for a third time for another 1½ hours and thawing at 55° C.

Following the freeze/thaw cycles described above, each of compositions Q, R, S, T, and U were clear and exhibited a thin viscosity.

TABLE 2

Compositions Q-S

| | Composition | | | | |
|---|---|---|---|---|---|
| | Q | R | S | T | U |
| Antimicrobial Organosilane Activity | 15% | 20% | 25% | 30% | 35% |
| N-alkyl,N,N dimethyl N benzylammonium chloride (grams) | 10 | 10 | 10 | 2 | 2 |

TABLE 2-continued

Compositions Q-S

| | Composition | | | | |
|---|---|---|---|---|---|
| | Q | R | S | T | U |
| diethylene glycol butyl ether (grams) | 100 | 100 | 100 | 20 | 20 |
| H₂0 (grams) | 285.98 | 251.3 | 216.63 | 36.39 | 29.46 |
| pH | 2.5 | 2.5 | 2.5 | 2.5 | 2.5 |
| 3-(trimethoxysilyl)propyl-dimethyloctadecyl ammonium chloride (grams) | 104.02 | 138.7 | 173.37 | 41.61 | 48.54 |

EXAMPLE 6

Dilution Studies

The effect of dilution on the stability of each of the compositions Q-U discussed in Example 5 was evaluated. 5 mls of each of compositions Q-U were mixed with 95 mls of H₂0. Diluted composition Q was clear and stable; no polymerization was observed. Diluted composition R was milky white, and some polymerization was observed. Diluted compositions S-U were milky white and polymerized almost immediately when the dilution water was added.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and the examples be considered as exemplary only, with the true scope and spirit of the invention being indicated by the claims.

It should be understood that the examples and embodiments described herein are for illustrative purposes only and that various modifications or changes in light thereof will be suggested to persons skilled in the art and are to be included within the spirit and purview of this application and the scope of the claims. All references cited herein, including journal articles or abstracts, published or unpublished patent application, issued patents or any other references, are entirely incorporated by reference herein, including all data, tables, figures and text presented in the cited references. Additionally, the entire contents of the references cited within the references cited herein are also entirely incorporated by reference.

We claim:

1. A composition comprising an organosilane and an acidic stabilizing solution:
wherein the organosilane is 3-(trimethoxysilyl)propyl-dimethyloctadecyl ammonium chloride; and
the acid stabilizing solution comprises at least one acid comprising hydrochloric acid, at least one glycol ether comprising diethylene glycol butyl ether, and at least one cationic surfactant in water, wherein the cationic surfactant is a quaternary ammonium salt having the following structure:

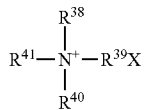

wherein each of $R^{38}$, $R^{39}$, $R^{40}$, and $R^{41}$ are independently selected from the group consisting of alkyl, aryl, and arylalkyl, or the nitrogen may be part of a ring system; and wherein X is an anion.

2. The composition according to claim 1, wherein the acidic stabilizing solution comprises exactly one acid, exactly one glycol ether, and exactly one cationic surfactant in water.

3. The composition according to claim 1, wherein at least one of $R^{38}$, $R^{39}$, $R^{40}$, or $R^{41}$ is an alkyl.

4. The composition according to claim 1, wherein the quaternary ammonium salt is an N-alkyl-N, N-Dimethyl-N-Benzyl ammonium chloride.

5. The composition according to claim 1, wherein the pH of the acidic stabilizing solution is between about 2 and about 3.

6. The composition according to claim 5, wherein the pH of the acidic stabilizing solution is about 2.5.

7. The composition according to claim 1, wherein the organosilane comprises from about 0.1 wt % to about 50 wt % of the composition.

8. A method for producing an antimicrobial organosilane composition according to claim 1, comprising:
a) mixing the at least one quaternary ammonium salt with the at least one glycol ether and water to produce a solution;
b) adding the at least one acid to the solution to acidify the solution; and
c) adding the solution to the organosilane.

9. The method according to claim 8, wherein at least one quaternary ammonium salt is an N-alkyl-N,N-Dimethyl-N-Benzyl ammonium chloride.

10. The method according to claim 8, comprising:
a) mixing exactly one quaternary ammonium salt with a glycol ether and water to produce a solution; and
b) adding exactly one acid to the solution to acidify the solution.

11. The method according to claim 8 wherein the pH of the solution after acidifying the solution is between about 2 and about 3.

12. The method according to claim 11, wherein the pH of the solution after acidifying the solution is about 2.5.

13. The method according to claim 8, wherein the organosilane comprises about 0.1 wt % to about 50 wt % of the antimicrobial organosilane composition.

14. The method according to claim 8, wherein the at least one quaternary ammonium salt comprises about 0.1 wt % to about 5 wt % of the solution.

15. The method according to claim 8, wherein the at least one glycol ether comprises about 5 wt % to about 20% of the solution.

16. A composition formed by mixing an organosilane and an acidic stabilizing solution:
wherein the organosilane is 3-(trimethoxysilyl)propyl-dimethyloctadecyl ammonium chloride; and
the acid stabilizing solution comprises at least one acid comprising hydrochloric acid, at least one glycol ether comprising diethylene glycol butyl ether, and at least one cationic surfactant in water, wherein the cationic surfactant is a quaternary ammonium salt having the following structure:

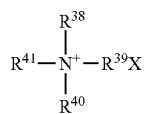

wherein each of $R^{38}$, $R^{39}$, $R^{40}$, and $R^{41}$ are independently selected from the group consisting of alkyl, aryl, and arylalkyl, or the nitrogen may be part of a ring system; and wherein X is an anion.

17. The composition according to claim 16, wherein at least one of $R^{38}$, $R^{39}$, $R^{40}$, or $R^{41}$ is an alkyl.

18. The composition according to claim 16, wherein the quaternary ammonium salt is an N-alkyl-N,N-Dimethyl-N-Benzyl ammonium chloride.

19. The composition according to claim 16, wherein the pH of the acidic stabilizing solution is about 2.5.

* * * * *

UNITED STATES PATENT AND TRADEMARK OFFICE
CERTIFICATE OF CORRECTION

PATENT NO. : 7,632,797 B2 Page 1 of 1
APPLICATION NO. : 11/680926
DATED : December 15, 2009
INVENTOR(S) : Timothy C. Moses and Robert McMahon It is certified that error appears in the above-identified patent and that said Letters Patent is hereby corrected as shown below:

Column 32,
Line 56 "about 20%" should read --about 20 wt%--.

Signed and Sealed this

Ninth Day of February, 2010

David J. Kappos
*Director of the United States Patent and Trademark Office*